United States Patent
Katoh et al.

(10) Patent No.: US 9,119,651 B2
(45) Date of Patent: Sep. 1, 2015

(54) RECANALIZING OCCLUDED VESSELS USING CONTROLLED ANTEGRADE AND RETROGRADE TRACKING

(75) Inventors: Osamu Katoh, Toyohashi (JP); Wayne Ogata, San Ramon, CA (US)

(73) Assignee: Retro Vascular, Inc., San Ramon, CA (US)

( * ) Notice: Subject to any disclaimer, the term of this patent is extended or adjusted under 35 U.S.C. 154(b) by 276 days.

(21) Appl. No.: 12/150,111

(22) Filed: Apr. 23, 2008

(65) Prior Publication Data

US 2008/0306499 A1 Dec. 11, 2008

Related U.S. Application Data

(63) Continuation-in-part of application No. 11/706,041, filed on Feb. 12, 2007, now Pat. No. 7,918,859.

(60) Provisional application No. 60/817,603, filed on Jun. 28, 2006, provisional application No. 60/773,357, filed on Feb. 13, 2006.

(51) Int. Cl.
*A61M 29/00* (2006.01)
*A61B 17/22* (2006.01)
(Continued)

(52) U.S. Cl.
CPC ............... *A61B 17/22* (2013.01); *A61B 17/221* (2013.01); *A61B 17/32075* (2013.01); *A61B 17/320725* (2013.01); *A61M 25/09* (2013.01); *A61B 17/22031* (2013.01); *A61B 19/54* (2013.01);
(Continued)

(58) Field of Classification Search
CPC ................... A61M 25/09; A61M 2025/09191; A61M 25/0043; A61M 25/0054; A61M 2025/09083; A61M 2025/09066; A61M 2025/09166; A61M 25/0069
USPC ......... 606/108, 191, 194, 198, 200; 623/1.11; 604/523–527, 170.01
See application file for complete search history.

(56) References Cited

U.S. PATENT DOCUMENTS 3,868,956 A 3/1975 Alfidi et al.
5,041,109 A 8/1991 Abela
(Continued)

FOREIGN PATENT DOCUMENTS

JP 2004500171 A 1/2004
JP 2006/263125 5/2006
(Continued)

OTHER PUBLICATIONS

Bourassa, Martial G. et al., "Bypass Angioplasty Revascularization Investigation: Patient Screening, Selection, and Recruitment", The American Journal of Cardiology, vol. 75, Issue 9, pp. 3C-8C, 1995.
(Continued)

*Primary Examiner* — Katherine M Shi
(74) *Attorney, Agent, or Firm* — LeClairRyan, a Professional Corporation

(57) ABSTRACT

A method and systems for treating chronic total occlusions, particularly those that are difficult to treat, is disclosed. In this approach, recanalizing the CTO is achieved using a combined antegrade and retrograde approach. The proximal end of the occlusion is penetrated using an antegrade wire, using a traditional approach. Using collateral vessels, the distal end of the occlusion is crossed in a retrograde fashion and by appropriately maneuvering each member, a continuous channel is created. Additional elements such as capture devices, dilators and injection catheters are also disclosed.

8 Claims, 24 Drawing Sheets

(51) Int. Cl.
| | |
|---|---|
| *A61B 17/221* | (2006.01) |
| *A61B 17/3207* | (2006.01) |
| *A61M 25/09* | (2006.01) |
| *A61B 19/00* | (2006.01) |
| *A61B 17/00* | (2006.01) |
| *A61M 25/00* | (2006.01) |

(52) U.S. Cl.
CPC ............... *A61B 2017/00685* (2013.01); *A61B 2017/00876* (2013.01); *A61B 2017/2212* (2013.01); *A61B 2017/22035* (2013.01); *A61B 2017/22044* (2013.01); *A61B 2017/22049* (2013.01); *A61B 2017/22061* (2013.01); *A61B 2017/22084* (2013.01); *A61B 2017/22094* (2013.01); *A61M 2025/0096* (2013.01); *A61M 2025/09091* (2013.01); *A61M 2025/09183* (2013.01)

(56) References Cited

U.S. PATENT DOCUMENTS

| | | | |
|---|---|---|---|
| 5,366,443 A | 11/1994 | Eggers et al. | |
| 5,419,767 A | 5/1995 | Eggers et al. | |
| 5,501,694 A * | 3/1996 | Ressemann et al. | 606/159 |
| 5,514,128 A | 5/1996 | Hillsman et al. | |
| 5,695,517 A | 12/1997 | Marin et al. | |
| 5,895,398 A | 4/1999 | Wensel et al. | |
| 6,068,645 A | 5/2000 | Tu | |
| 6,235,044 B1 | 5/2001 | Root et al. | |
| 6,416,523 B1 | 7/2002 | Lafontaine | |
| 6,454,775 B1 | 9/2002 | Demarais et al. | |
| 6,697,863 B1 | 2/2004 | Egawa | |
| 6,911,026 B1 | 6/2005 | Hall et al. | |
| 6,936,056 B2 | 8/2005 | Nash et al. | |
| 7,037,316 B2 | 5/2006 | McGuckin, Jr. et al. | |
| 7,918,859 B2 | 4/2011 | Katoh et al. | |
| 2002/0058939 A1 | 5/2002 | Wagner et al. | |
| 2003/0028200 A1* | 2/2003 | Berg et al. | 606/108 |
| 2004/0082879 A1* | 4/2004 | Klint | 600/585 |
| 2004/0082962 A1 | 4/2004 | Demarais et al. | |
| 2004/0230219 A1 | 11/2004 | Roucher, Jr. | |
| 2005/0154400 A1* | 7/2005 | Kato et al. | 606/127 |
| 2005/0171478 A1 | 8/2005 | Selmon et al. | |
| 2005/0228431 A1* | 10/2005 | Meguro et al. | 606/194 |
| 2006/0079880 A1 | 4/2006 | Sage et al. | |
| 2006/0224112 A1* | 10/2006 | Lentz | 604/96.01 |
| 2007/0043389 A1 | 2/2007 | Shindelman | |
| 2007/0049867 A1 | 3/2007 | Shindelman | |
| 2007/0083132 A1* | 4/2007 | Sharrow | 600/585 |
| 2007/0112342 A1 | 5/2007 | Pearson et al. | |
| 2007/0208368 A1 | 9/2007 | Katoh et al. | |
| 2008/0039935 A1 | 2/2008 | Buch et al. | |
| 2008/0306499 A1 | 12/2008 | Katoh et al. | |
| 2010/0256616 A1 | 10/2010 | Katoh et al. | |
| 2010/0292685 A1 | 11/2010 | Katoh et al. | |

FOREIGN PATENT DOCUMENTS

| | | |
|---|---|---|
| JP | 2007-195599 | 8/2007 |
| WO | 00/09020 | 2/2000 |
| WO | 0139673 A1 | 6/2001 |
| WO | 2009042614 A1 | 4/2009 |

OTHER PUBLICATIONS

Colombo, Antonio et al., "Treating Chronic Total Occlusions Using Subintimal Tracking and Reentry: The STAR Technique", Catheterization and Cardiovascular Interventions, vol. 64, No. 4, pp. 407-411, 2005.

Ito, Shigenori et al., "Novel Technique Using Intravascular Ultrasound-Guided Guidewire Cross in Coronary Intervention for Uncrossable Chronic Total Occlusions", Circulation Journal, vol. 68, No. 11, pp. 1088-1092, Nov. 2004.

Kimura, Bruce J. et al., "Subintimal Wire Position During Angioplasty of a Chronic Total Coronary Occlusion: Detection and Subsequent Procedural Guidance by Intravascular Ultrasound", Catheterization and Cardiovascular Diagnosis, vol. 35, No. 3, pp. 262-265, 1995.

King, Spencer B. et al., "A Randomized Trial Comparing Coronary Angioplasty with Coronary Bypass Surgery. Emory Angioplasty versus Surgery Trial (EAST)", The New England Journal of Medicine, vol. 331, No. 16, pp. 1044-1050, Oct. 20, 1994.

Kinoshita, Isao et al., Coronary Angioplasty of Chronic Total Occlusions With Bridging Collateral Vessels: Immediate and Follow-Up Outcome From a Large Single-Center Experience, Journal of the American College of Cardiology, vol. 26, No. 2, pp. 409-415, Aug. 1995.

Matsubara, Tetsuo et al., "IVUS-Guided Wiring Technique: Promising Approach for the Chronic Total Occlusion", Catheterization and Cardiovascular Interventions, vol. 61, No. 3, pp. 381-386, 2004.

Melchior, Jean-Paul et al., "Improvement of Left Ventricular Contraction and Relaxation Synchronism After Recanalization of Chronic Total Coronary Occlusion by Angioplasty", Journal of the American College of Cardiology, vol. 9, No. 4, pp. 763-768, Apr. 1987.

Olivari, Zoran et al., "Immediate Results and One-Year Clinical Outcome After Percutaneous Coronary Interventions in Chronic Total Occlusions: Data From a Multicenter, Prospective, Observational Study (TOAST-GISE)", Journal of the American College of Cardiology, vol. 41, No. 10, pp. 1672-1678, 2003.

Suero, James A. et al., "Procedural Outcomes and Long-Term Survival Among Patients Undergoing Percutaneous Coronary Intervention of a Chronic Total Occlusion in Native Coronary Arteries: A 20-Year Experience", Journal of the American College of Cardiology, vol. 38, No. 2, pp. 409-414, 2001.

International Search Report and Written Opinion for International Application No. PCT/US07/03706, mailed Sep. 22, 2008.

International Search Report and Written Opinion for International Application No. PCT/US2008/077403, mailed Dec. 1, 2008.

International Search Report and Written Opinion for International Application No. PCT/US2009/041287, mailed Jul. 7, 2009.

Office Action for Canadian Application No. 2,641,729, dated May 14, 2010.

Office Action in U.S. Appl. No. 11/706,041, mailed May 12, 2010.

Notice of Allowance in U.S. Appl. No. 11/706,041, mailed Nov. 26, 2010.

Korean Non-Final Rejection for Korean Application No. 10-2008-7022167, dated Nov. 23, 2010.

Australian Office Action in Australian Application No. 2007215224, dated Apr. 8, 2010.

Australian Office Action in Australian Application No. 2008304599, dated Feb. 22, 2011.

International Search Report and Written Opinion in International Application No. PCT/2011/031018, mailed Jun. 14, 2011.

Canadian Office Action in Canadian Application No. 2,641,729, dated Feb. 28, 2011.

European Search Report (Extended) in European Application No. 09734649.8, mailed Feb. 24, 2011.

Japanese Office Action in Japanese Application No. 2008-554416, mailed May 31, 2011.

Bolia, A. et al. "Recanalization of Iliac Artery Occlusion by Subintimal Dissection Using the Ipsilateral and the Contralateral Approach," Clinical Radiology, vol. 52, 1997, pp. 684-687.

Spinosa, D. J. et al. "Simultaneous Antegrade and Retrograde Access for Subintimal Recanalization of Peripheral Arterial Occlusion," Journal of Vascular and Interventional Radiology, vol. 14, Issue 11, Nov. 2003, pp. 1449-1454.

Feb. 22, 2011 Examination Report issued on Australian Patent Application No. 2008304599 issued by the Australian Patent Office, pp. 1-4.

Jul. 20, 2012 Filed Response to Feb. 22, 2011 Examination Report issued on Australian Patent Application No. 2008304599, pp. 1-20.

Sep. 4, 2012 Examination Report issued on Australian Patent Application No. 2008304599 issued by the Australian Patent Office, pp. 1-4.

(56) References Cited

OTHER PUBLICATIONS

Oct. 11, 2012 Filed Response to Sep. 4, 2012 Second Examination Report issued on Australian Patent Application Serial No. 208304599, pp. 1-7.
Mar. 1, 2012 Examination Report issued on Australian Patent Application No. 2009239406 issued by the Australian Patent Office, pp. 1-2 Abandoned.
May 25, 2012 Office Action issued by Canadian Patent Office on Canadian Patent Application No. 2,722,486, pp. 1-3.
Nov. 23, 2012 Filed Response to May 25, 2012 Office Action issued by Canadian Patent Office on Canadian Patent Application No. 2,722,486, pp. 1-4.
May 14, 2010 Office Action issued by Canadian Patent Office on Canadian Patent Application No. 2,641,729, pp. 1-3.
Nov. 15, 2010 Filed Response to May 14, 2010 Office Action issued by Canadian Patent Office on Canadian Patent Application No. 2,641,729, pp. 1-13.
Feb. 28, 2011 Office Action issued by Canadian Patent Office on Canadian Patent Application No. 2,641,729, pp. 1-3.
Aug. 22, 211 Filed Response to Feb. 28, 2011 Office Action issued by Canadian Patent Office on Canadian Patent Application No. 2,641,729, pp. 1-24.
Jan. 12, 2012 Office Action issued by Canadian Patent Office on Canadian Patent Application No. 2,641,729, pp. 1-3.
Jul. 11, 2012 Filed Response to Jan. 12, 2012 Office Action issued by Canadian Patent Office on Canadian Patent Application No. 2,641,729, pp. 1-9.
Jul. 24, 2012 Extended Supplementary European Search Report, issued by the European Patent Office for European patent application serial No. 08834456.9, pp. 1-9.
Nov. 19, 2012 Filed Response to Jul. 24, 2012 Extended Supplementary European Search Report, issued by the European Patent Office for European patent application serial No. 08834456.9, pp. 1-10.
Feb. 24, 20111 Supplementary European Search Report, issued by the European Patent Office for European patent application serial No. 09734649.8, pp. 1-6.
Sep. 26, 2011 Filed Response to Feb. 24, 2011 Search Opinion issued by the European Patent Office for European patent application serial No. 09734649.8, pp. 1-8.
Nov. 23, 2011 Examination Report issued by the European Patent Office for European patent application serial No. 09734649.8, pp. 1-3.
Feb. 7, 2012 European Associates's Comments in reply to Communication Pursuant to Article 94(3) issued by the European Patent Office for European patent application serial No. 09734649.8, pp. 1-2.
Jun. 4, 2012 File Response to Nov. 23, 2011 Examination Report issued by the European Patent Office for European patent application serial No. 09734649.8, pp. 1-4.
Dec. 10, 2012 Decision to Refuse European Application issued by the European Patent Office for European patent application serial No. 09734649.8, pp. 1-8.
May 31, 2011 Office Action issued by Japanese Patent Office on Japanese Patent Application No. 2008-554416, pp. 1-4.
Jul. 26, 2011 Filled Response to May 31, 2011 Office Action issued by Japanese Patent Office on Japanese Patent Application No. 2008-554416, pp. 1-3.
Mar. 28, 2012 Certificate of Patent issued Feb. 24, 2012 by Japanese Patent Office on Japanese Patent Application No. 2008-554416, pp. 1-3.
Jun. 15, 2012 Notice of Reason for Rejection issued by Japanese Patent Office on Japanese Patent Application No. 2011-506400, pp. 1-8.
Sep. 17, 2012 Instructions for Response to Jun. 15, 2012 Notice of Reason for Rejection (Decision of Rejection) issued by Japanese Patent Office on Japanese Patent Application No. 2011-506400, pp. 12.
Nov. 6, 2012 Decision of Rejection issued by Japanese Patent Office on Japanese Patent Application No. 2011-506400, pp. 1-5.
Dec. 27, 2012 Foreign Associates Comments on Nov. 6, 2012 Decision of Rejection issued by Japanese Patent Office on Japanese Patent Application No. 2011-506400, pp. 1-6.
Nov. 23, 2010 Non-Final Rejection issued by Korean Patent Office on Korean Application No. 10-2008-7022167 pp. 1-6.
Jan. 24, 2011 Filed Response to Nov. 23, 2010 Non-Final Rejection issued by Korean Patent Office on Korean Application No. 10-2008-7022167 pp. 1-26.
Jul. 20, 2011 Notice of Allowance issued by Korean Patent Office on Korean Application No. 10-2008-7022167 pp. 1-3.
May 18, 2012 Instructions for Response to Dec. 19, 2011 Non-Final Rejection issued by Korean Patent Office on Korean Application No. 10-2010-7008803 pp. 1-5.
Oct. 29, 2012 Notice of Allowance issued by Korean Patent Office on Korean Application No. 10-2010-7008803 pp. 1-3.
Sep. 22, 2008 International Search Report for PCT Application No. PCT/US2007/03706, pp. 1-2.
Oct. 21, 2008 International Preliminary Report on Patentability with Written Opinion issued on PCT Application No. PCT/US2007/003706, pp. 1-4.
Dec. 1, 2008 International Search Report issued for PCT Application No. PCT/US2008/077403, p. 1.
Jul. 7, 2009 International Search Report Issued for PCT Application No. PCT/US2009/041287, pp. 1-2.
Jun. 14, 2011 International Search Report and Written Opinion issued on PCT Application No. PCT/US2011/031018, pp. 1-7.
Feb. 13, 2013 Office Action for U.S. Appl. No. 12/753,844, pp. 1-15.
Feb. 4, 2013 Office Action for U.S. Appl. No. 13/037,304, pp. 1-15.

* cited by examiner

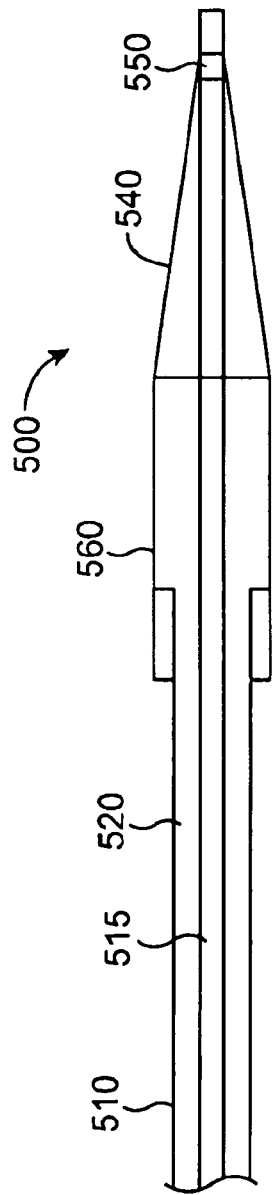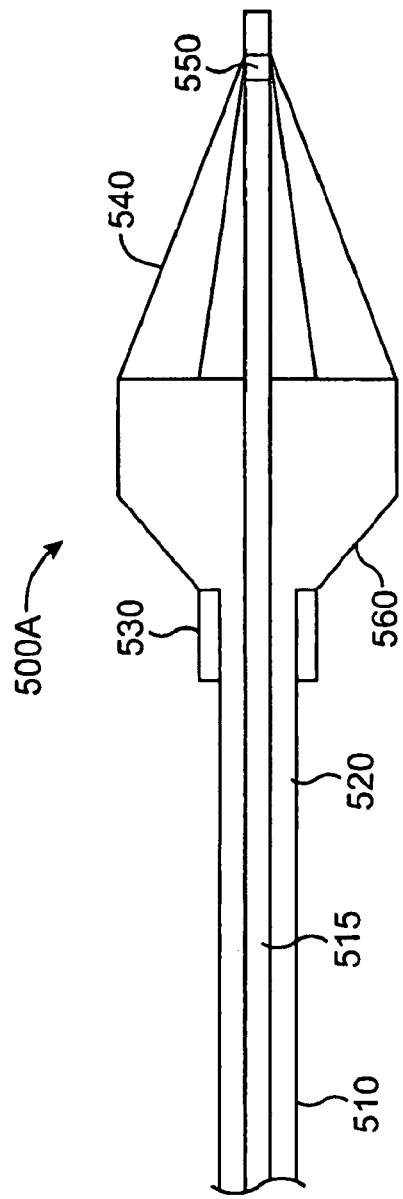

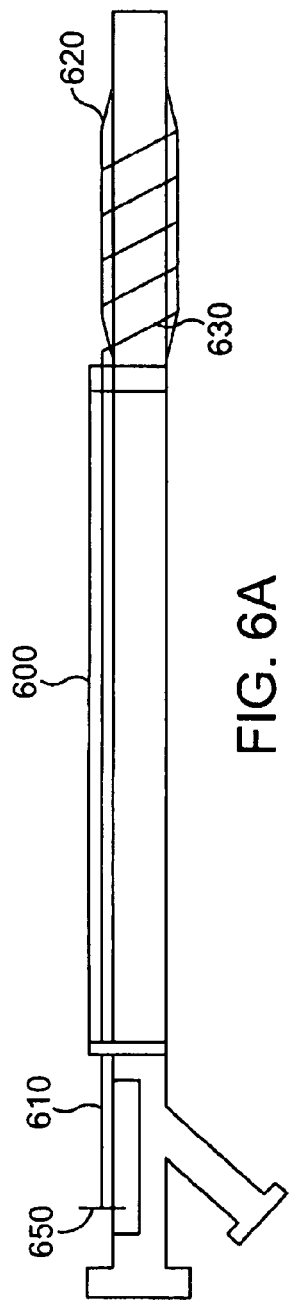
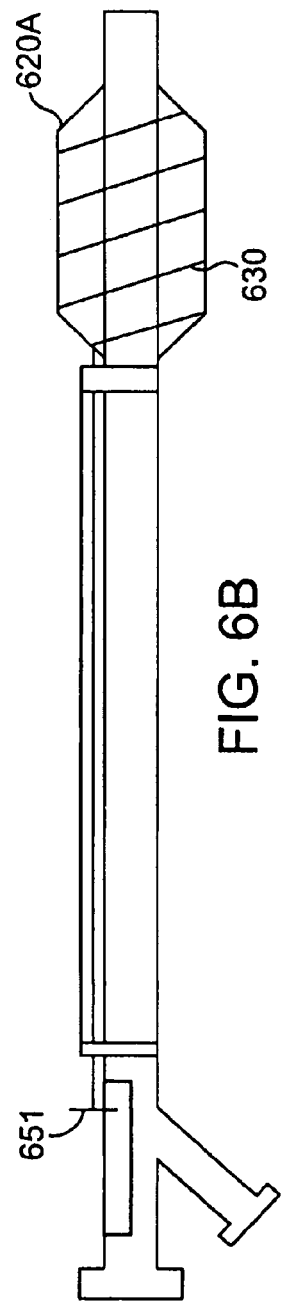
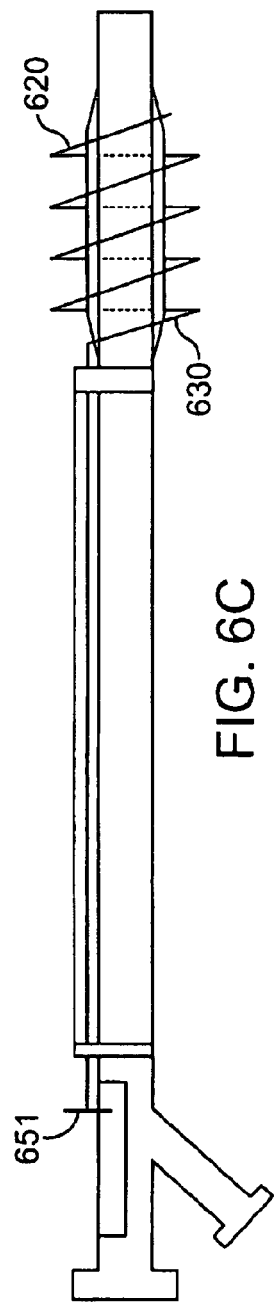
FIG. 6A
FIG. 6B
FIG. 6C

RECANALIZING OCCLUDED VESSELS USING CONTROLLED ANTEGRADE AND RETROGRADE TRACKING

CROSS-REFERENCES TO RELATED APPLICATIONS

This application is a continuation in part of application Ser. No. 11/706,041, filed on Feb. 12, 2007, which claims the benefit and priority of the following: U.S. Provisional Application Ser. No. 60/773,357, filed on Feb. 13, 2006 and U.S. Provisional Application Ser. No. 60/817,603, filed on Jun. 28, 2006, the full disclosures of which are incorporated herein by reference.

FIELD OF THE INVENTION

This invention relates generally to catheters and more specifically to catheter apparatus and methods for treating severe or total chronic occlusions of lumens in the body.

DESCRIPTION OF THE RELATED ART

Chronic total occlusion (CTO) is the complete blockage of a vessel and usually has serious consequences if not treated in a timely fashion. The blockage could be due to atheromatous plaque or old thrombus. One of the common procedures for treating CTOs of the coronary arteries is percutaneous transluminal coronary angioplasty (PTCA). During a PTCA procedure, a small incision is, typically, made in the groin. A guiding catheter over a guide wire is introduced into the femoral artery and advanced to the occlusion. Frequently, with gentle maneuvering, the guidewire is able to cross the stenosis. Then, a balloon-tipped angioplasty catheter is advanced over the guide wire to the stenosis. The balloon is inflated, separating or fracturing the atheroma. Some of the common steps involved in the PTCA procedure are the simultaneous injection of a contrast agent in the contra-lateral vessel, getting backup force or stabilization for a guide wire (which could invoke additional personnel to handle the catheter), puncturing the plaque, drilling or rotating the guide wire to push it through the dense plaque, etc. Because of the stiff resistance sometimes offered by dense plaque, one could be forced to use stiff wires. Occasionally, the wires could puncture the vessel wall calling for remedial measures.

Percutaneous treatment of coronary chronic total occlusions remains one of the major challenges in interventional cardiology. Recent data have shown that successful percutaneous recanalization of chronic coronary occlusions results in improved survival, as well as enhanced left ventricular function, reduction in angina, and improved exercise tolerance (Melchior J P, Doriot P A, Chatelain P, et al. Improvement of left ventricular contraction and relaxation synchronism after recanalization of chronic total coronary occlusion by angioplasty. *J Am Coll Cardiol.* 1987; 9(4):763-768; Olivari Z, Rubartelli P, Piscione F, et al. Immediate results and one-year clinical outcome after percutaneous coronary interventions in chronic total occlusions: data from a multicenter, prospective, observational study (TOAST-GISE). *J Am Coll Cardiol.* 2003; 41(10):1672-1678; Suero J A, Marso S P, Jones P G, et al. Procedural outcomes and long-term survival among patients undergoing percutaneous coronary intervention of a chronic total occlusion in native coronary arteries: a 20-year experience. *J Am Coll Cardiol.* 2001; 38(2):409-414).

However, because of the perceived procedural complexity of angioplasty in CTOs, it still represents the most common reason for referral to bypass surgery, or for choosing medical treatment (Bourassa M G, Roubin G S, Detre K M, et al. Bypass Angioplasty Revascularization Investigation: patient screening, selection, and recruitment. *Am J Cardiol.* 1995; 75(9):3C-8C; King S B, 3rd, Lembo N J, Weintraub W S, et al. A randomized trial comparing coronary angioplasty with coronary bypass surgery. Emory Angioplasty versus Surgery Trial (EAST). *N Engl J Med.* 1994; 331(16):1044-1050.)

The most common percutaneous coronary intervention (PCI) failure mode for CTOs is inability to successfully pass a guidewire across the lesion into the true lumen of the distal vessel (Kinoshita I, Katoh O, Nariyama J, et al. Coronary angioplasty of chronic total occlusions with bridging collateral vessels: immediate and follow-up outcome from a large single-center experience. *J Am Coll Cardiol.* 1995; 26(2): 409-415). To date, there is no consensus on how best to treat CTO after attempts with conventional guidewires have failed. Different strategies and specific devices for CTOs have been developed including the subintimal tracking and reentry with side branch technique, parallel wire technique, IVUS guided technique, and retrograde approach (Colombo A, Mikhail G W, Michev I, et al. Treating chronic total occlusions using subintimal tracking and reentry: the STAR technique. *Catheter Cardiovasc Interv.* 2005; 64(4):407-411; discussion 412; Ito S, Suzuki T, Ito T, et al. Novel technique using intravascular ultrasound-guided guidewire cross in coronary intervention for uncrossable chronic total occlusions. *Circ J.* 2004; 68(11):1088-1092; Kimura B J, Tsimikas S, Bhargava V, et al. Subintimal wire position during angioplasty of a chronic total coronary occlusion: detection and subsequent procedural guidance by intravascular ultrasound. *Cathet Cardiovasc Diagn.* 1995; 35(3):262-265; Matsubara T, Murata A, Kanyama H, et al. IVUS-guided wiring technique: promising approach for the chronic total occlusion. *Catheter Cardiovasc Interv.* 2004; 61(3):381-386). However, none of these alternate strategies have provided satisfactory results for the most challenging of the CTOs.

Hence, it could be beneficial to have alternate techniques and devices that would recanalize a CTO without the shortcomings of the current techniques. CTOs that are hard to recanalize, either because of the tortuous anatomy of the diseased vessel, or because the proximal end of the stenosis is too hard for the guide wire to penetrate, or other characteristics of the CTO that would make the standard procedure vulnerable to failure would benefit from newer approaches to recanalize CTOs.

SUMMARY OF THE INVENTION

Various methods and devices are provided to overcome some of the commonly encountered problems in treating chronic total occlusions. One aspect of this invention is to provide a method and systems for successfully recanalizing an occluded vessel by advancing, in combination, guidewires in an antegrade and retrograde fashion to the occlusion.

A method of recanalizing an occluded vessel comprising advancing in an antegrade fashion a first longitudinal member through a proximal end of an occlusion, advancing in a retrograde fashion a second longitudinal member through a distal end of the occlusion, and creating a continuous channel between the proximal and distal ends of the occlusion.

In another aspect, this invention relates to a catheter assembly for recanalizing an occluded vessel comprising an antegrade longitudinal member with a distal end that is capable of being advanced through the proximal end of the occlusion, a retrograde longitudinal member with a distal end that is capable of being advanced through the distal end of the occlusion; and the distal ends of the antegrade longitudinal member and retrograde longitudinal member cooperate to form a continuous channel inside the occluded vessel.

In another embodiment of this invention, a catheter assembly for recanalizing an occluded vessel comprising an antegrade longitudinal member with a distal end that is capable of being advanced through the proximal end of the occlusion, a retrograde longitudinal member with a distal end that is capable of being advanced through the distal end of the occlusion, the distal end of the retrograde longitudinal member having proximal and distal tips that are connected by compressible elements, wherein advancing one tip towards the other enables the compressible elements to flare out and form a capture mechanism. Upon deploying the compressible elements of the distal end of the retrograde member, advancing the antegrade member results in the antegrade member being engaged in the deployed capture mechanism, and pulling one end of the retrograde distal end from the other retracts the compressible elements, enabling the combined antegrade and retrograde members to be pulled back into the proximal or distal lumen.

Yet another embodiment of this invention is a catheter assembly for recanalizing an occluded vessel comprising an antegrade longitudinal member with a distal end that is capable of being advanced through the proximal end of the occlusion, a retrograde longitudinal member with a distal end that is capable of being advanced through the distal end of the occlusion, the distal end of the antegrade longitudinal member having proximal and distal tips that are connected by compressible elements, and advancing one tip towards the other enables the compressible elements to flare out and form a capture mechanism. Upon deploying the compressible elements at the distal end of the antegrade member, further advancing the retrograde member results in the retrograde member being engaged in the deployed capture mechanism, and pulling one end of the antegrade distal end from the other collapses the compressible elements, enabling the combined antegrade and retrograde members to be pulled back into the proximal or distal lumen.

In another embodiment, the invention is a kit for recanalizing occluded vessels comprising one or more of the following: an antegrade guidewire, a retrograde guidewire, a dilating device, a capture device and an injection catheter.

Other aspects of the invention include methods corresponding to the devices and systems described above. Additionally, the invention includes ancillary devices that enable or assist the delivery of the catheter assembly including, but not limited to, an injection catheter to aid in the visualization of the arteries or to deliver a therapeutic agent to the treatment site, a dilating catheter to help create and maintain a channel, and a retrograde guidewire.

BRIEF DESCRIPTION OF THE DRAWINGS

The invention has other advantages and features which will be more readily apparent from the following detailed description of the invention and the appended claims, when taken in conjunction with the accompanying drawings, in which:

FIGS. 5A through 5F show embodiments of capture devices in their deployed and undeployed states. FIGS. 5A and 5B illustrate one embodiment of the capture device in its undeployed (FIG. 5A) and deployed (FIG. 5B) states. FIGS. 5C and 5D show an example of another such capture device with the capture mechanism (basket) deployed (FIG. 5C) and the antegrade guidewire captured in the basket (FIG. 5D). FIGS. 5E and 5F illustrate another embodiment of the capture device in the undeployed and deployed states, respectively.

FIGS. 6A through 6E show another embodiment of the capture device that includes an angioplasty balloon.

DETAILED DESCRIPTION OF THE PREFERRED EMBODIMENTS

Figure 1:
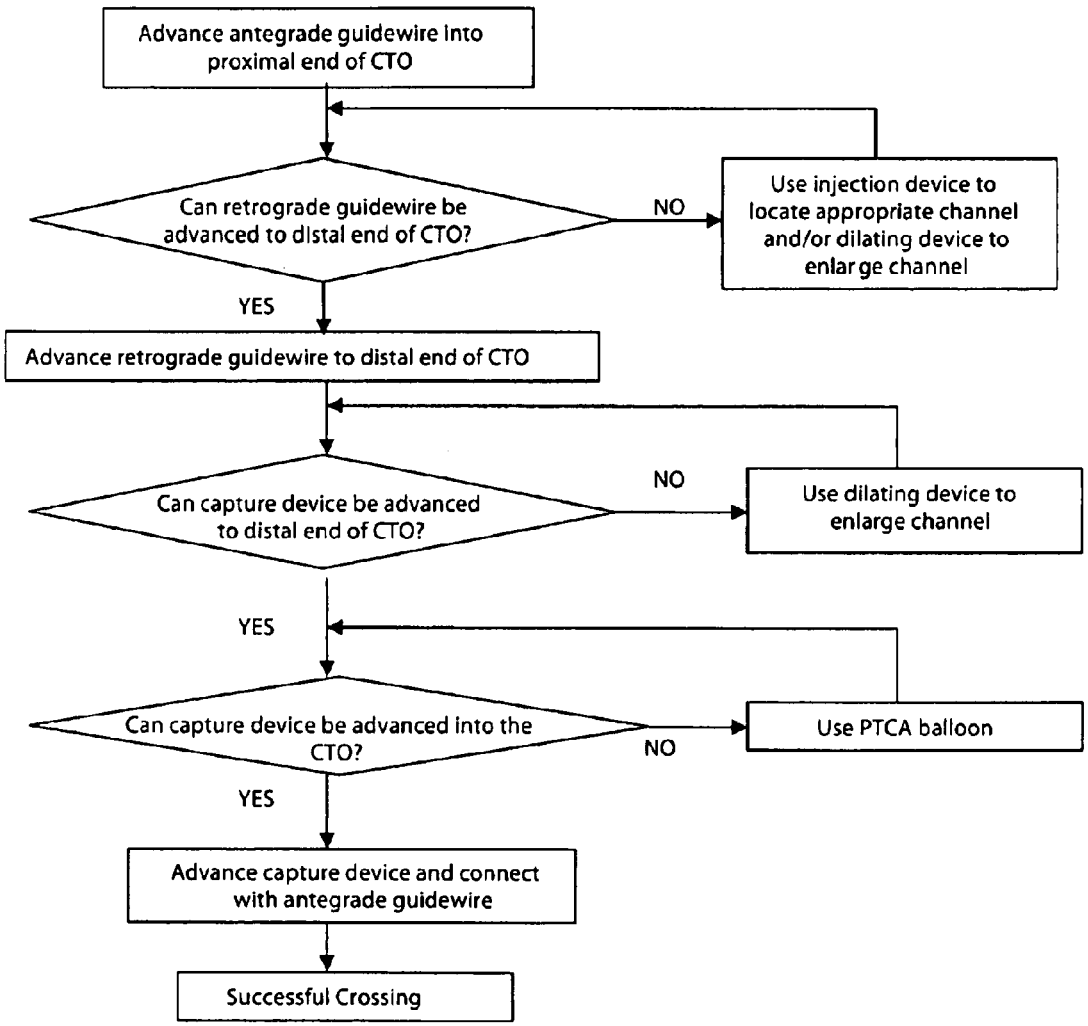
FIG. 1 is a schematic showing the different steps involved in the recanalization technique.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as described here.

This invention combines the use of controlled antegrade and retrograde tracking (CART) approaches for recanalizing occluded lumens, particularly chronic total occlusions. The retrograde approach takes advantage of an intercoronary channel, which can be either an epicardial channel, interatrial channel, an intra-septal channel (also referred to as septal collateral), or a bypass graft. Careful review of the angiogram usually allows one to find a septal channel in most CTO cases, particularly in the LAD or RCA. The basic concept of the CART technique is to create a channel through an occlusion, preferably with limited dissections, by approaching the occlusion both antegradely and retrogradely. Once a channel is formed, a guidewire can be placed through the occlusion and the lesion can be treated in a conventional manner.

The general concept for practicing the CART technique is as follows: advance an antegrade longitudinal member up to the proximal end of the occlusion. Advance a retrograde longitudinal member up to the distal end of the occlusion. Advance both members through the occlusion until they approach each other and create a continuous channel through the occlusion. This process can be facilitated by enlarging the channel and providing a means for one longitudinal member to capture and either push or pull the other longitudinal member across the occlusion. The enlarging mechanism can be any number of designs including, but not limited to, balloon dilatation, drilling, flaring ribs and others known in the art such as a vibrating longitudinal member (for example, the CROSSER™ high frequency ultrasound vibration device from FlowCardia, Inc. of Sunnyvale, Calif.), an oscillating or rotating longitudinal member (for example, the rotating or oscillating guidewire from Revascular Therapeutics of Sunnyvale, Calif.), a blunt dissection catheter (for example, the FRONTRUNNER® XP CTO Catheter from Cordis Endovascular, Inc.), a radio frequency (RF) longitudinal member (for example, the Safe-Cross® wire from Kensey Nash of Exton, Pa.), a support catheter (for example, the Quick-Cross® support catheter from Spectranetics Corp. of Colorado Springs, Colo.), or a wire for delivering transverse ultrasonic energy along its length (for example, the Omni-Wave® wire from OmniSonics Medical Technologies, Inc. of Wilmington, Mass.). The capturing mechanism can also be any number of designs including, but not limited to, flaring ribs, coils and balloons, in which one member actually snares the other longitudinal member, or a basket or net which allows passage for the other longitudinal member through the occlusion. Upon traversing the occlusion, the longitudinal member may need to be extended to allow delivery of a subsequent therapeutic device. The longitudinal member can be a guidewire, a microcatheter, a catheter or the like.

A flowchart depicting the process steps in practicing the CART technique is shown in FIG. 1. The antegrade guidewire is advanced to the proximal end of the occlusion and the retrograde wire is advanced to the distal end of the occlusion through an appropriate septal. Occasionally, the septals are not easily identified. In such cases, an injection catheter is used to inject contrast to locate the vessels and the appropriate septal that could be used for the retrograde approach is identified. The retrograde guidewire and capture device are now advanced to the CTO. In case of difficulty in advancing the retrograde wire, a special septal dilator tool is used to enlarge the septal lumen and then a capture device is advanced through the occlusion. The antegrade guidewire is now advanced through the lesion and brought to the location of the capture device, which is then deployed. In case there is difficulty in deploying the capture device, a PTCA balloon is used to enlarge the lumen at the appropriate location, the capture device is then deployed and the antegrade guidewire is captured by the device attached to the retrograde guidewire. The total occlusion is thereby successfully crossed.

Figure 2:
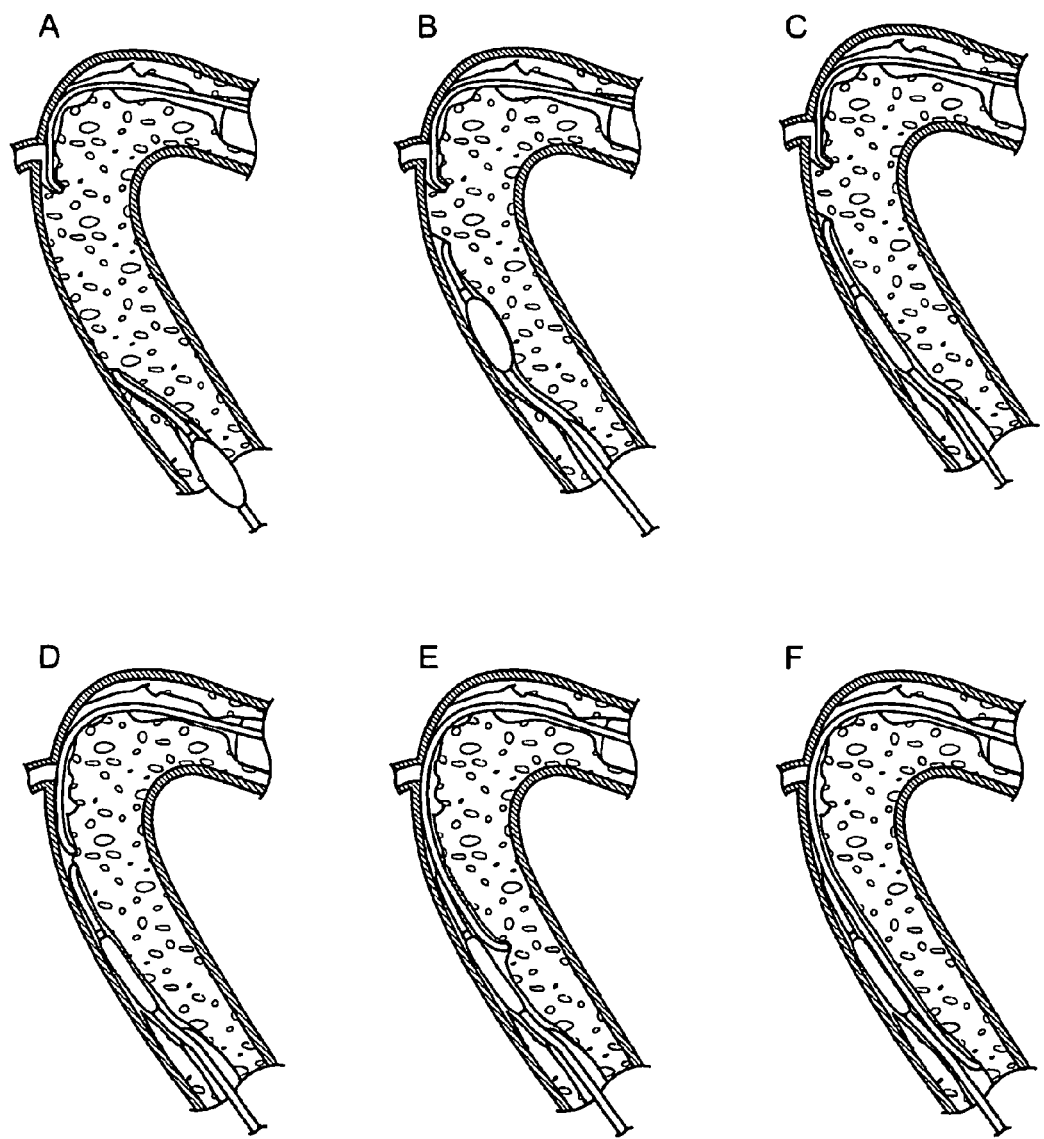
FIGS. 2A through 2F are pictorial illustrations of the CART technique.

The above steps are illustrated in FIGS. 2A-2F. As shown in FIG. 2A, first, a guidewire is advanced antegradely from the proximal true lumen into the CTO and then into the subintimal space at the CTO site. Next, another guidewire is advanced through the intercoronary collateral using a microcatheter. A micro-catheter helps to protect the channel from injury and achieve better wire maneuverability. This guidewire is placed at the distal end of the CTO, and then penetrates retrogradely from the distal true lumen into the CTO, and then into the subintima at the CTO site (FIG. 2A). After advancing a small balloon (1.5-2.0 mm) over the retrograde guidewire into the subintima, the balloon is inflated, creating a dissection plane that extends into the distal end of the CTO (FIG. 2B). In order to keep this subintimal space open, the deflated balloon is left in place (FIG. 2C). Consequently, the two dissections created by the antegrade wire and the retrograde balloon lay in the subintima at the CTO site, which allows them to connect easily (FIG. 2D). Thereafter, the antegrade wire is advanced further along the space created by the deflated retrograde balloon (FIGS. 2E and 2F). In FIG. 2F, the antegrade wire is advanced through the channel created by the retrograde wire into the distal true lumen. This technique allows a limited dissection situated only in the portion of the CTO lesion, and avoids the difficulty of reentering the distal true lumen. After successful recanalization, dilatation and stent implantation are performed. Typical materials recommended for the retrograde approach are summarized in Table 1.

Figure 3:
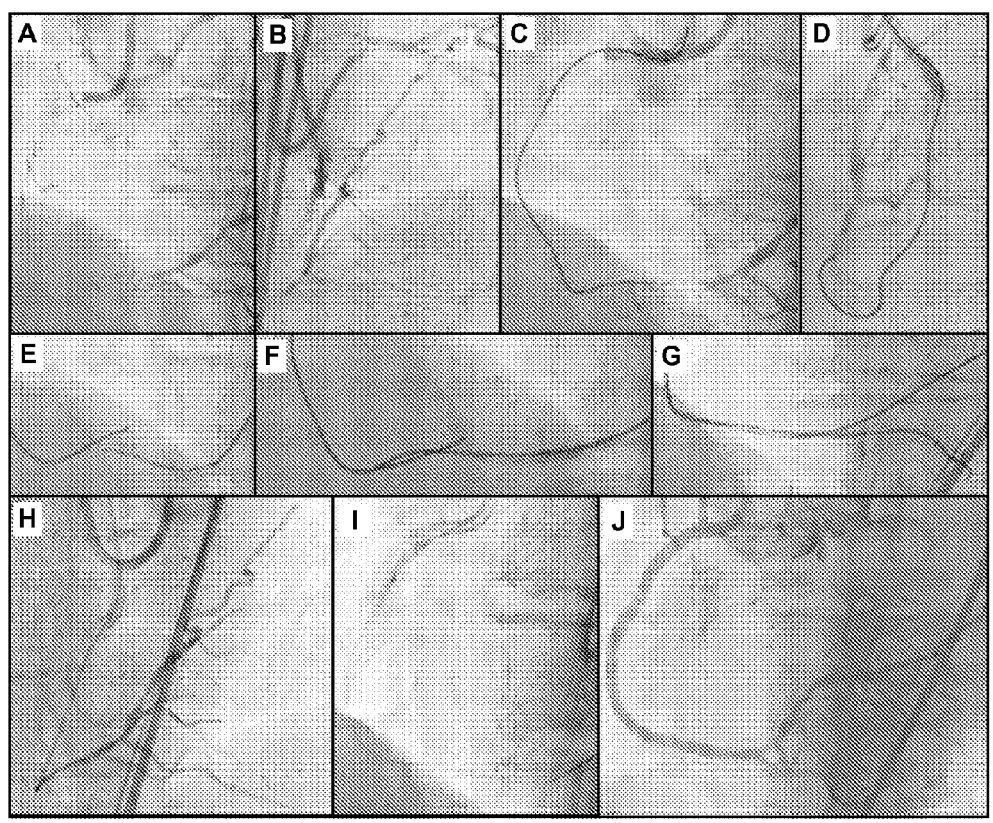
FIG. 3 contains angiograms that illustrate the CART technique.
Figure 4:
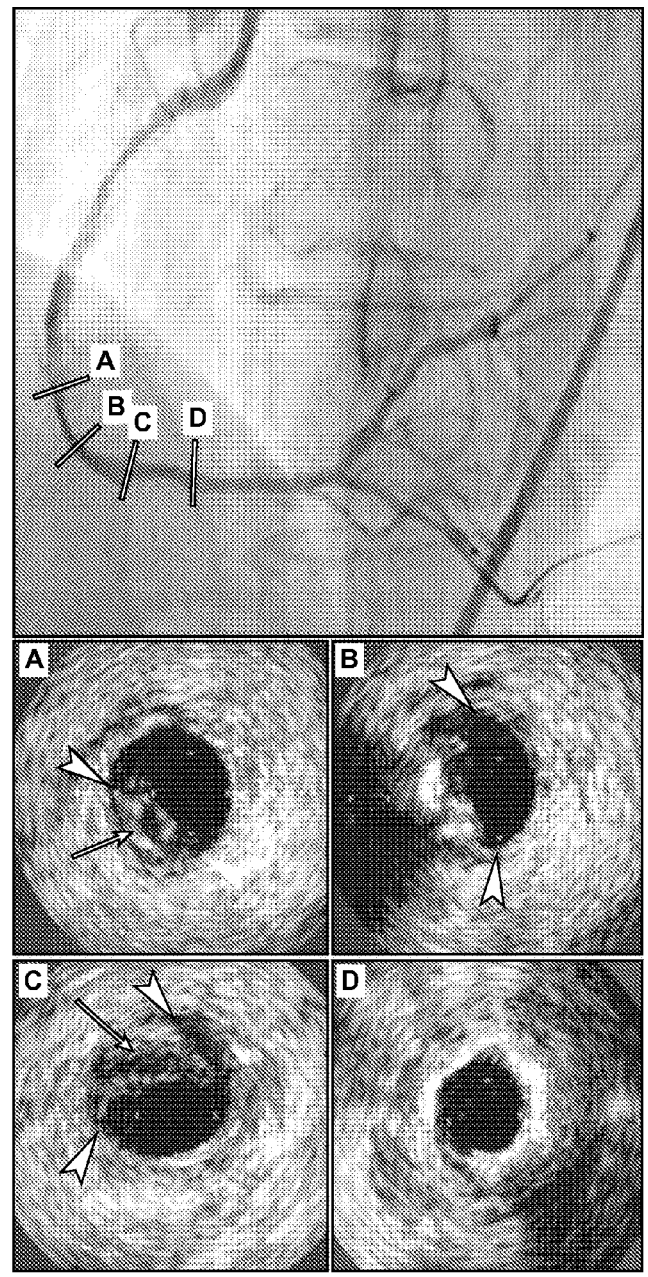
FIG. 4 displays IVUS images for the example shown.

FIGS. 3 and 4 show a clinical example of the implementation of the claimed recanalization technique. The CTO characteristics are well demonstrated by a bilateral coronary injection (FIG. 3A: LAO view; FIG. 3B: LAO-cranial view). This long CTO was old (>72 months), had an abrupt onset, moderate calcification, and bridging collaterals. In FIGS. 3C and 3D, the antegrade wire was advanced into the subintimal space of the CTO without success while trying to reenter the distal true lumen. In FIG. 3E the retrograde wire penetrated the distal end of the CTO. FIG. 3F shows further advancement of the retrograde wire and balloon dilatation of the subintimal space. FIG. 3G shows that the antegrade wire easily found the subintimal space created by the retrograde wire, and then was advanced into the distal true lumen. In FIG. 3H the retrograde wire was then retrieved. A bilateral coronary injection confirmed the correct position of the antegrade wire in the distal true lumen. FIG. 3I shows the antegrade sequential balloon dilatation and FIG. 3J shows the final angiographic result after stent implantation.

FIG. 4 shows the IVUS images for the above example. Sequential images illustrating the passage from the subintimal space (A, B and C) to the distal true lumen (D). The arrowheads show the extension of the large subintimal dissection. The arrows show the CTO tissue lying adjacent to the dissection.

Figure 5B:
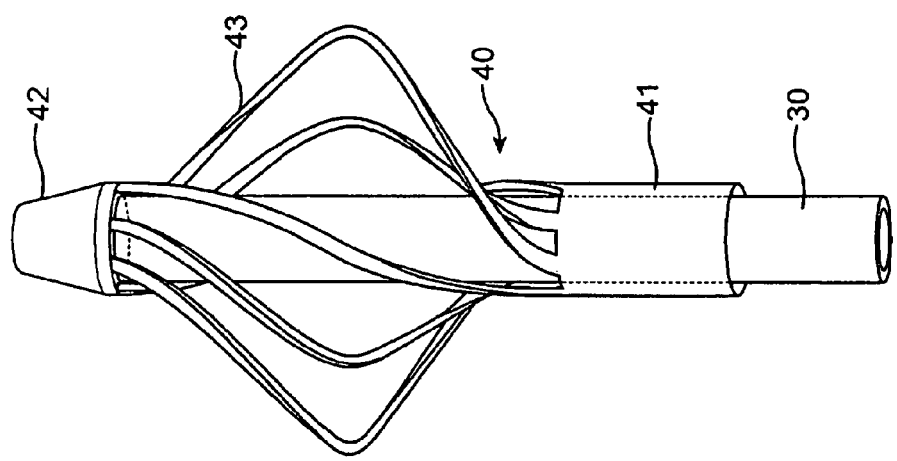
Figure 5A:
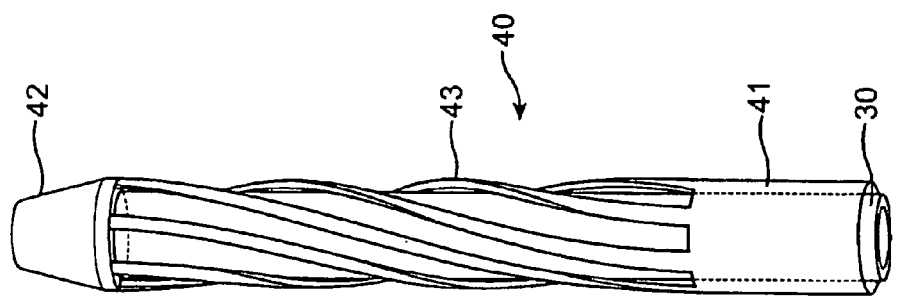

Various types of capture devices are envisaged in working the present invention. FIG. 5A shows one embodiment of the claimed invention. A slidable sleeve 40 is disposed on the distal end of a tubular member 30. Tubular member 30 could be, but is not necessarily, a microcatheter, a guidewire, or a balloon catheter. Sleeve 40 has a proximal end 41, a distal end 42 and a plurality of ribs 43. The distal end 42 is fixed to the distal end of the tubular member 30 using commonly known techniques. When the proximal end 41 is pushed towards the distal end 42 or by pulling the distal end 42 towards the operator (pulling back the inner shaft), the ribs flare out like a basket, as shown in FIG. 5B.

Figure 5C:
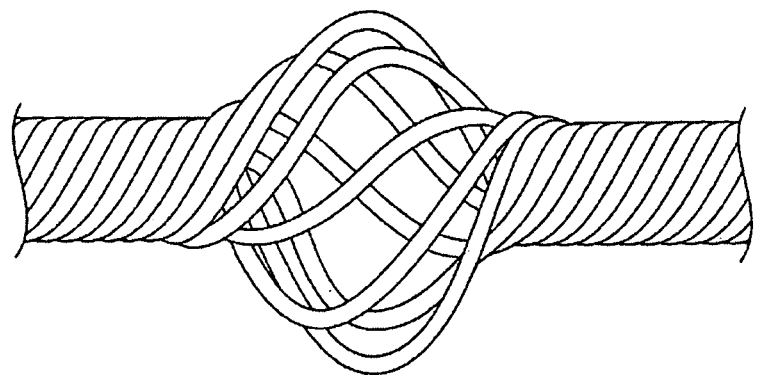
Figure 5D:
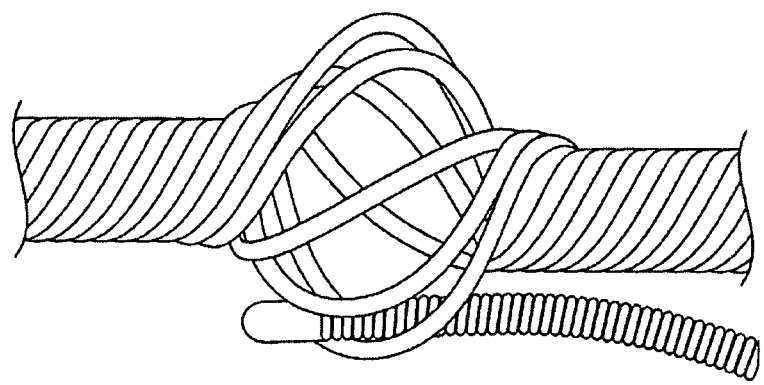

Another embodiment of the capture device is shown in FIGS. 5C and D, where twistable wires are used to create a basket-like structure for capturing the guide wire that is advanced in the retrograde or antegrade fashion. FIG. 5C shows the capture device in its deployed state. Well-known mechanisms can be used to twist the wires at one end resulting in the basket-like opening at the desired location. This enables the guide wire that has been advanced in the opposite direction to be captured in the basket-like opening. The twistable wires are flared out (deployed) into a basket-like structure as shown in FIG. 5D to capture the end of the guidewire. Untwisting the wires collapses the basket to its original state enabling the combined capture device and guide wire to be maneuvered to create a continuous channel. The wires could be made of materials commonly used in catheter and guidewire manufacture, such as stainless steel, platinum, tantalum, titanium, Elgiloy or nitinol. Nitinol wires would be particularly attractive as they can have low profile in their undeployed state and can be deployed by using either force or temperature. Well-known mechanisms can be used to twist the wires at one end resulting in the basket-like opening at the desired location. This enables the guide wire that has been advanced in the opposite direction to be captured in the basket-like opening. Now, untwisting the wires collapses the basket to its original state enabling the combined capture device and guide wire to be maneuvered to create a continuous channel.

Yet another embodiment of the capture device is shown in FIGS. 5E and 5F. The device 500 comprises a catheter shaft 510, a guidewire lumen 515, and a capture lumen 520. These two lumens could be either coaxial or side-by-side. The distal end of the catheter shaft comprises tension wires 540, which are anchored at the distal tip 550 of the guidewire lumen 515. The wires and the stop 530, which is attached at the distal end of the catheter shaft 510 but proximal to anchor location 550, form basket 560, which is used to capture the antegrade or retrograde guidewires by funneling the guidewire into the capture lumen 520. In FIG. 5E, the basket 560 is shown in its low profile (collapsed) state, where the tension wires 540 are kept under tension, for example, by twisting the basket or by using a restraining sleeve (not shown). The catheter, with the basket in its collapsed state, is advanced into the occlusion over a guidewire. Upon releasing the tension or pulling back on the restraining sleeve, the basket flares open, as shown in 500A. Once the basket is open, the antegrade or retrograde guidewire is advanced and funneled into the basket and through the capture lumen of the capture device.

The basket itself can be made of a mesh-like structure or ribs made of an elastic alloy such as Nitinol and covered with either a non-porous material or a semi-porous material such as polytetrafluoroethylene (PTFE) or Dacron with pores large enough to allow some blood flow but small enough to not entangle the guidewire.

In another embodiment, the guidewire lumen 515 can alternatively be a stiffening wire, which acts as a guidewire. In yet another example, the capture lumen 520 would be the original guidewire lumen used to advance the capture device to the occlusion.

Figure 5G:
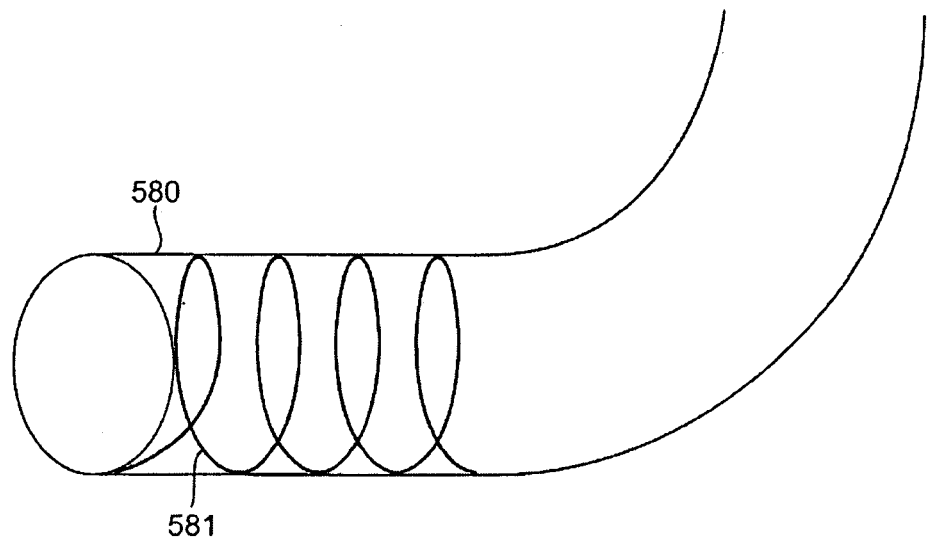
FIGS. 5G through 5N show other embodiments of the capture device in compressed and expanded states.
Figure 5H:
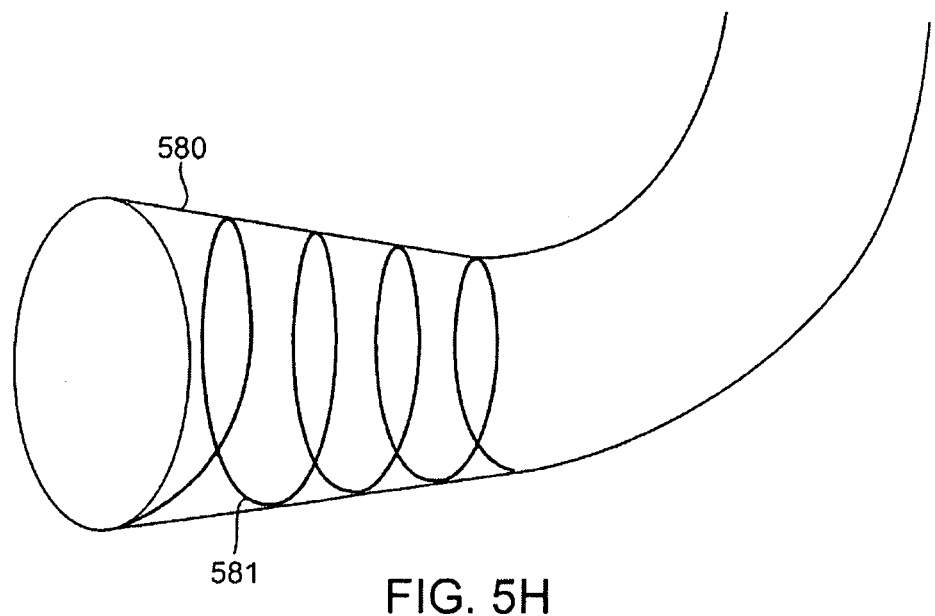
Figure 5I:
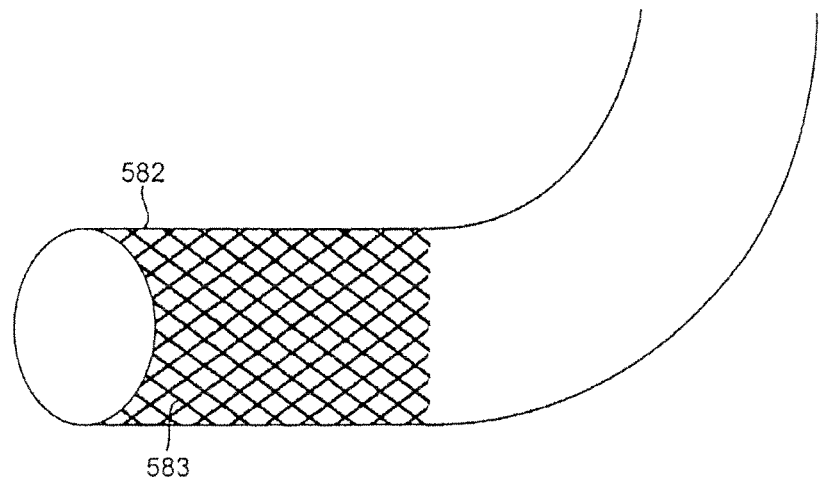
Figure 5J:
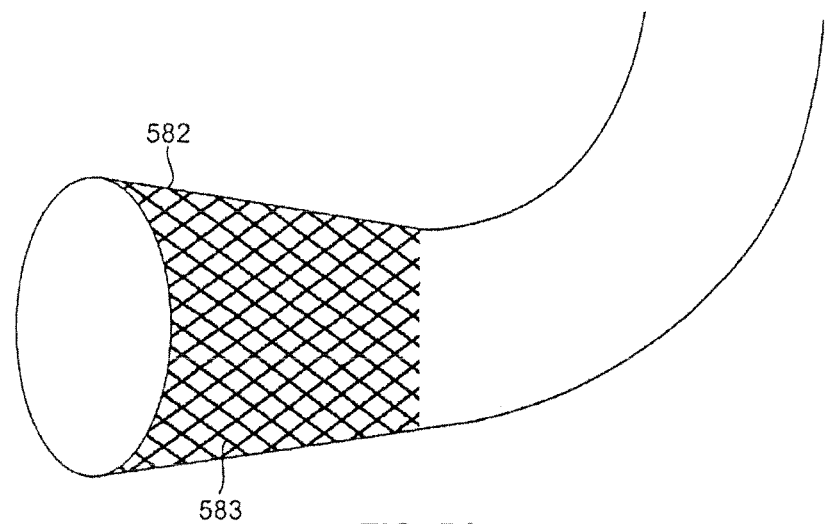
Figure 5K:
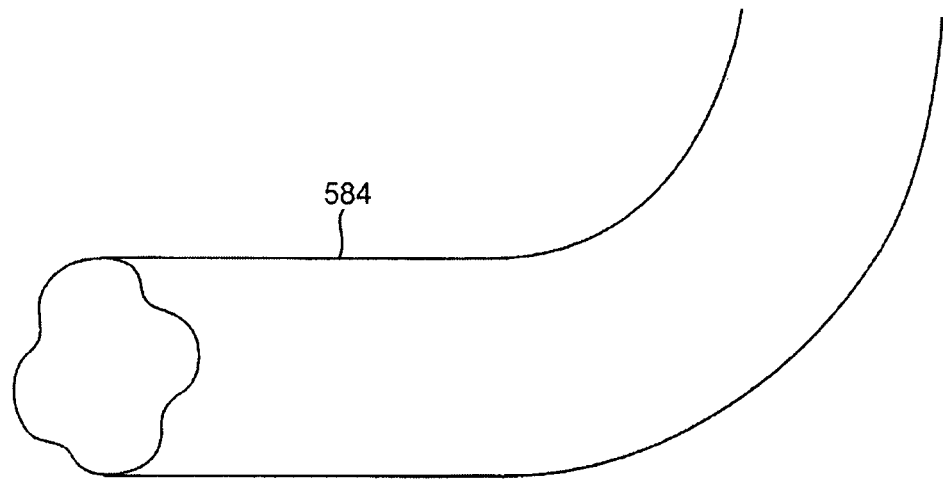
Figure 5L:
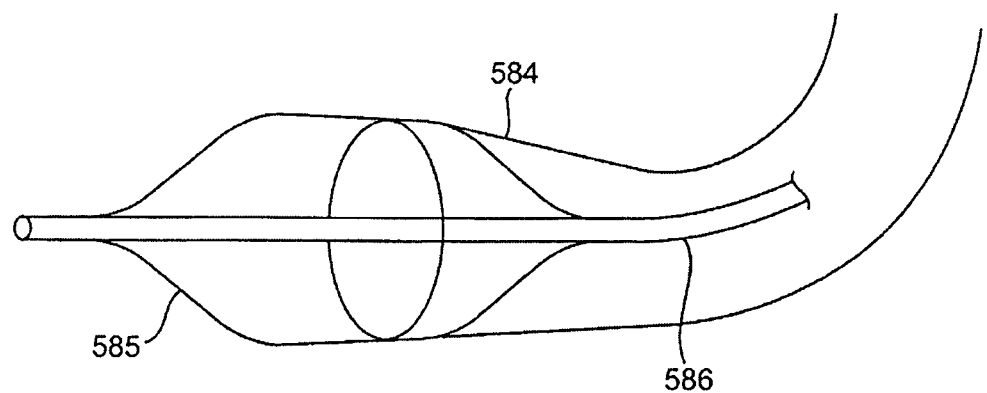

In other embodiments of the capture device, the distal end of the capture device is expandable and acts as a funnel or narrowing passageway to accept a guidewire or catheter that has been advanced in the opposite direction. Numerous distal end designs which allow for expansion of the distal end may be employed, including but not limited to: uncoiling of a coiled member of the distal end to cause expansion of the distal end (as shown in FIGS. 5G and 5H); realignment of a mesh-like portion of the distal end, whereby as the mesh is held in tension it retains a lower profile than when the mesh is in a relaxed state, or vice versa (as shown in FIGS. 5I and 5J); a star-like configuration of the distal end which can be caused to flare to a larger diameter (as shown in FIGS. 5K and 5L); by using one or more openings or incisions in the wall of the distal end of the capture device; or by using an expandable material such as expanded polytetrafluoroethylene (ePTFE) for the distal end of the capture device. FIGS. 5G through 5L illustrate some examples of such embodiments.

FIGS. 5G and 5H show an exemplary embodiment of a distal end 580 of a capture device comprising a coil 581. In FIG. 5G, coil 581 is in a state where tension is retained in the coil 581. In FIG. 5H, the coil 581 is in a partially uncoiled state where some of the tension is released from the coil 581, causing the distal end 580 to flare open to receive a guidewire. Retention and release of tension in the coil 581 may be achieved by manual or automatic rotational action at the proximal end of the capture device (not shown), wherein rotation in one direction may release coil tension and rotation in an opposite direction may increase coil tension, thereby causing the distal end 580 to expand or contract, respectively. Alternatively, coil 581 may be configured to behave in the opposite manner, i.e., to expand under increased tension and contract when tension is released.

FIGS. 5I and 5J show an exemplary embodiment of a distal end 582 of a capture device comprising a mesh 583. The mesh 583 may be constructed, for example, of a shape-memory material such as Nitinol and configured to expand in the absence of compression. In FIG. 5I, mesh 583 is in its compressed state. FIG. 5J shows mesh 583 is in its uncompressed state, expanded outwards and open to receive a guidewire.

FIGS. 5K and 5L show an exemplary embodiment of a distal end 584 of a capture device comprising a star-like configuration which can flare to a larger diameter. Initially, the distal end 584 is in an unflared state, as shown in FIG. 5K. Forward movement and/or expansion of a separate inner member, for example an inflated balloon 585 of a balloon catheter 586, as shown in FIG. 5L, causes expansion or flaring of the distal end 584 to a larger diameter.

Figure 5M:
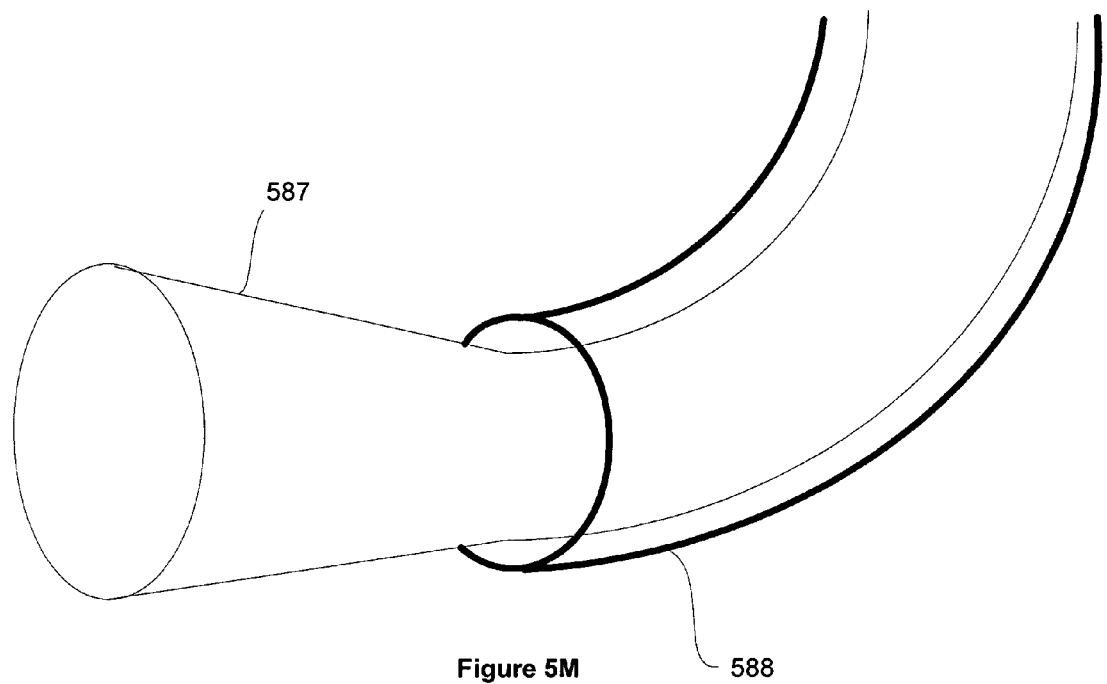
Figure 5N:
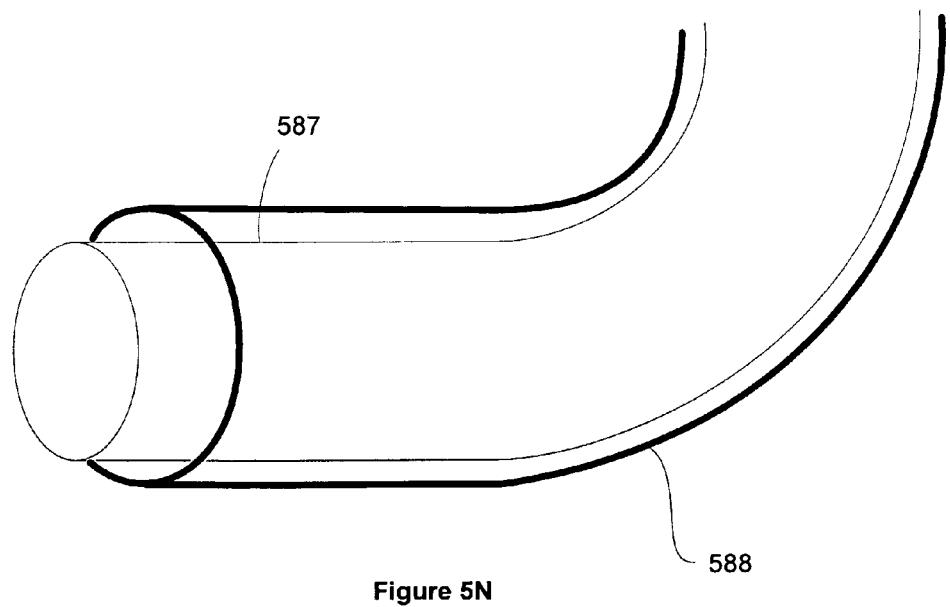

Alternatively, compression of the distal end of a capture device may be accomplished by a separate outer sheath configured to selectively cover or expose the distal end. Such an embodiment is shown in FIG. 5M. The distal end 587 is allowed to expand as the sheath 588 pulls back to expose the distal end 587, and it is compressed as the sheath 588 advances forward to cover the distal end 587 (FIG. 5N). In yet other embodiments, the expansion or flaring of the distal end of the capture device may be induced mechanically, thermally, chemically, or electrically, as will be obvious to those of ordinary skill in the art. Note that the capture device embodiments can independently be used as standard guiding catheters. One advantage is the use of a smaller profile sheath introducer, as well as being able to engage a small or stenosed ostium with a larger guide.

Another embodiment of the capture device is shown in FIGS. 6A-6C. Catheter 600 is similar to a standard PTCA or PTA balloon catheter. Balloon 620 is at the distal end of the catheter. A wire 610 is wound around the balloon 620. When the trigger is in its pulled back position 650, wire 610 is tightly wound around the balloon (coiled at the distal end and shown as 630). When the trigger is advanced to 651 and the balloon expanded, coil 630 is in its expanded state. At the start of the procedure, trigger 650 is in its pulled back, locked position. This keeps 630 tightly wrapped around balloon 620 and provides a very low profile balloon and enables easy delivery of the balloon 620 to the desired location. If the catheter 600 is used as the retrograde longitudinal member, upon locating the balloon as shown in FIG. 2D, the trigger is advanced to its forward location 651. The balloon is then expanded using standard means to achieve its inflated state 620A, which expands the distal section of the wire. Upon compacting the plaque against the vessel wall, the balloon is deflated to its original state 620. The distal section of the wire now remains in its expanded state, similar to the deployed state of the capture devices shown in FIG. 5B, 5C, or 5F. The antegrade wire is now advanced, which is then captured in the expanded wire. Following this capture, the trigger is now reverted to the pulled back position 650. This allows the antegrade and retrograde wire to cooperate with each other to form a continuous channel.

As can be understood, the catheter 600 could also be advanced in an antegrade fashion to capture a guidewire that is advanced in a retrograde fashion. Similar to the method described above for using the catheter 600 in a retrograde fashion, catheter 600 is advanced to the desired location with the wire 610 wound around the balloon 620 and thus presenting a low profile balloon. Upon reaching the desired location, the trigger is released and the balloon is inflated. After compacting the plaque against the vessel wall, the balloon is deflated, but the wire remains in its expanded state. The retrograde guidewire is then advanced and captured in the expanded distal part of wire 610. The trigger is then set in its pulled back position 650 resulting in the antegrade catheter and retrograde guidewire cooperating to form a continuous channel in the lesion.

Figure 6D:
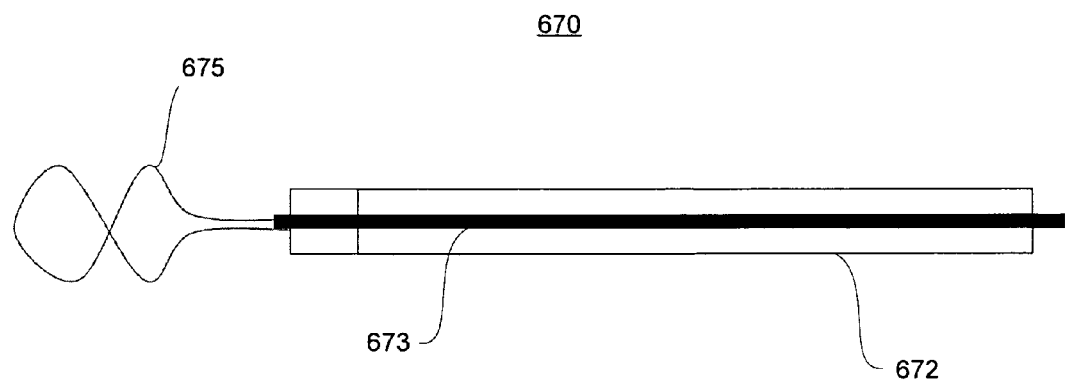
Figure 6E:
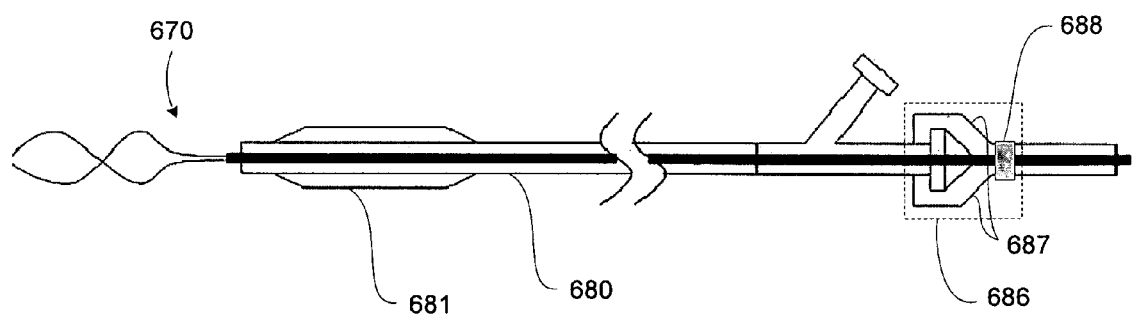

Alternatively, a capture device may comprise an expandable capture wire configuration, contained within a catheter lumen, for capturing a guidewire. FIGS. 6D and 6E show two such embodiments. In FIG. 6D, a capture wire configuration 670 comprises an expandable capture wire 675 attached to a shaft 673 and configured to advance distally out of a catheter 672 lumen. The capture wire 675 expands as it leaves the lumen, ready to capture a guidewire, as shown in FIG. 6D. Once a guidewire is within the capture wire 675, the capture wire configuration 670 is pulled back into the catheter lumen, collapsing the capture wire 675 as it retreats, and capturing and pulling the guidewire in the process. The capture wire 675 may comprise a shape-memory material, causing the wire to expand as it advances out of the catheter. Generally, capture wire 675 is sheathed within the catheter lumen prior to reaching the treatment site, and is exposed and deployed upon reaching the treatment site. Alternatively, the catheter may comprise an inflatable balloon. FIG. 6E shows an exemplary balloon catheter 680 comprising an inflatable balloon 681 and a capture wire configuration 670 contained within the catheter lumen. Optionally, the expandable capture wire configuration 670 is rotatable.

Optionally, any of the catheters comprising a capture device may also comprise a locking tool which is used to secure the capture wire configuration to the catheter so that the guidewire is firmly captured and can then be pulled through the lesion. FIG. 6E shows an exemplary use of a torque device 686 at the proximal end of the catheter 680. A number of designs typically seen in standard torque devices can be employed as part of this locking tool including but not limited to compressible prongs, screws, and a slidable ring. In one embodiment of the locking device, a number of compressible prongs 687 are longitudinally aligned with and placed over the shaft of the capture wire configuration. The prongs 687 are surrounded by a wheel or ring 688 which when rotated, squeezes down on the prongs 687 and reduces its inner diameter. The prongs are also designed such that their distal end can latch onto the hub of the catheter. As the wheel 688 is rotated, the prongs 687 lock onto both the capture wire configuration and catheter so as to form a single unit. It should be noted that the locking device 686 can also act as a standard torque device used to aid guidewire manipulations.

In an optional embodiment, any of the capture devices described above may comprise a filter to capture debris released from the occlusion during the course of the medical procedure, thereby inhibiting transportation of such debris through the blood stream to other parts of the body and, in particular, prevent embolization. The filter may be attached at any point along the length of the capture device. The filter may comprise any number of designs, including but not limited to a basket or net, a flat mesh, prongs or wire strands around a shaft, a coil, a polymer sheet with holes, or a balloon. Optionally, any of the capture devices described herein may comprise a mechanism to extract debris via suction, for example by using a suction device inline with the capture device.

Figure 6F:
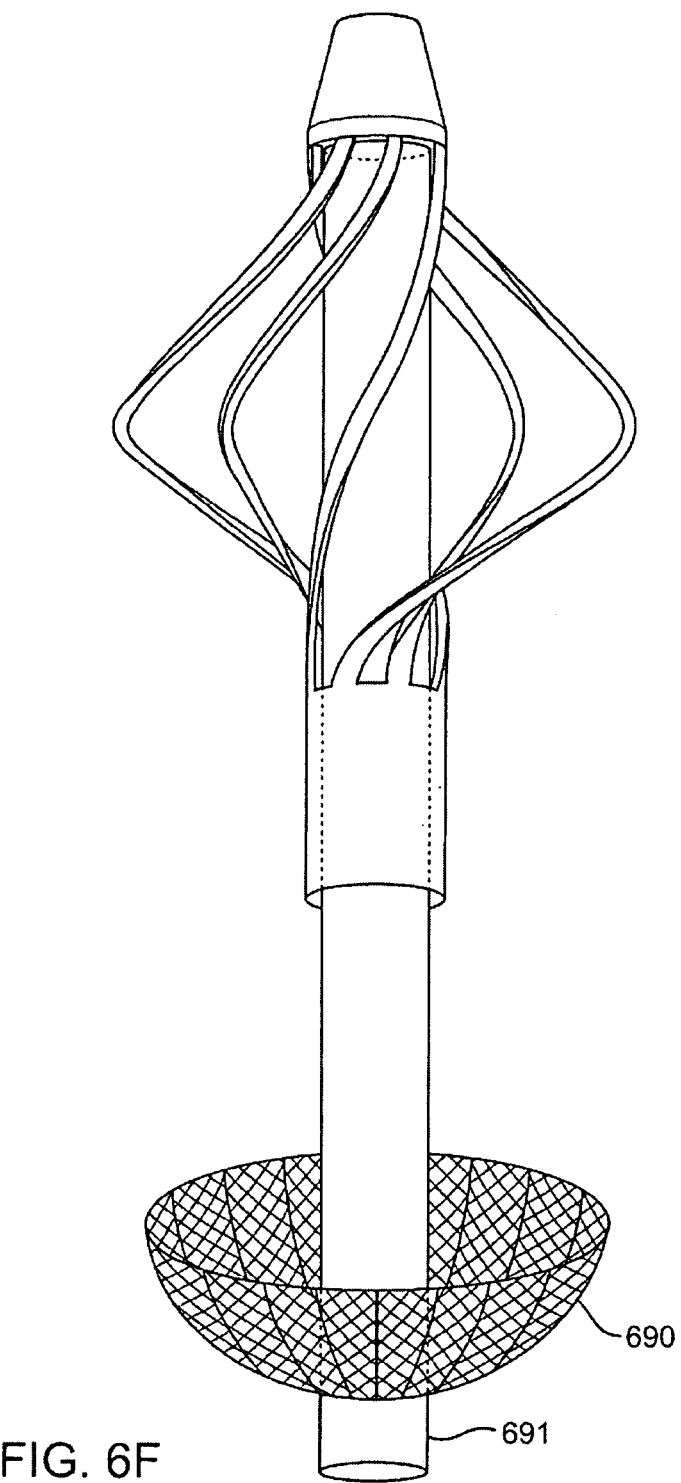
FIG. 6F shows an embodiment of the capture device comprising a filter device.

FIG. 6F shows an exemplary net filter 690 in a deployed state at the proximal edge of a capture device 691. Generally, the filter 690 is in a compressed state around the capture device shaft during transport through the vasculature. The filter 690 is then deployed or expanded (as shown) at the treatment site to capture debris released from the occlusion. For example, a separate outer member or sheath may be used to compress the filter 690 during delivery, and to deploy the filter at the treatment site by retracting the outer member or sheath to expose the filter 690. Optionally, the same outer member may be used to deploy both the capture device and the filter 690.

Figure 7B:
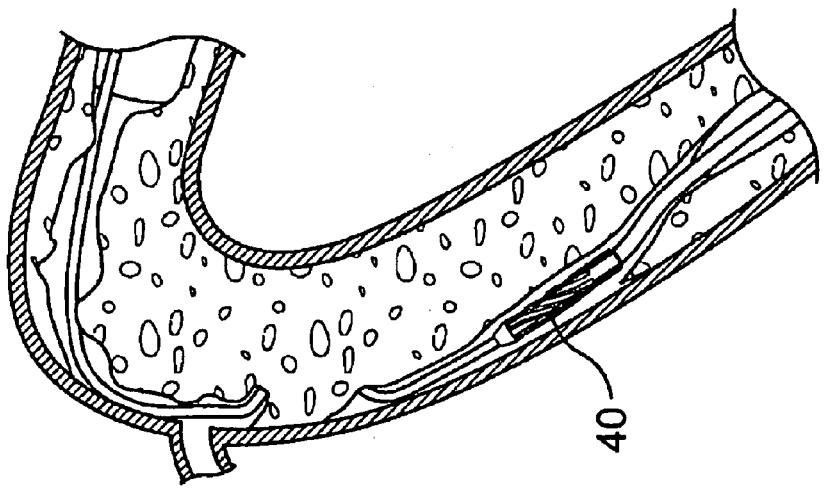
FIGS. 7A through 7F illustrate the CART technique using a capture device.
Figure 7A:
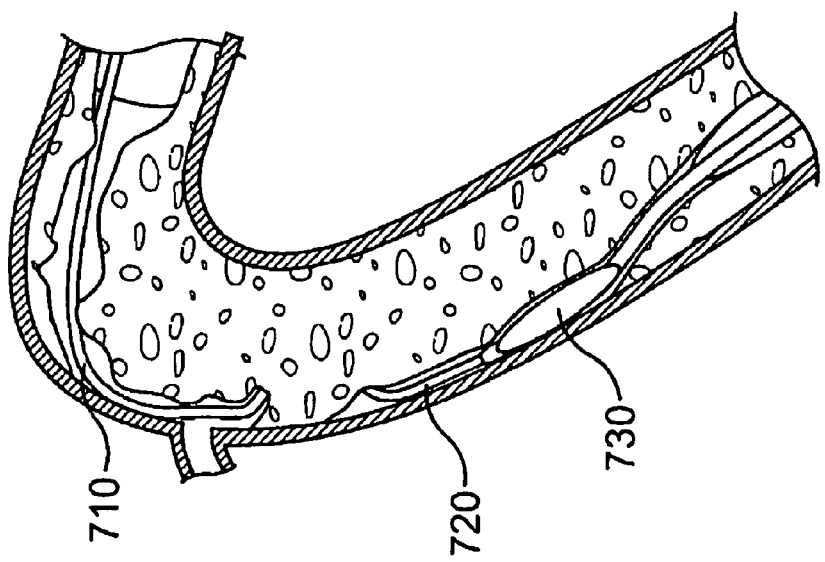
Figure 7D:
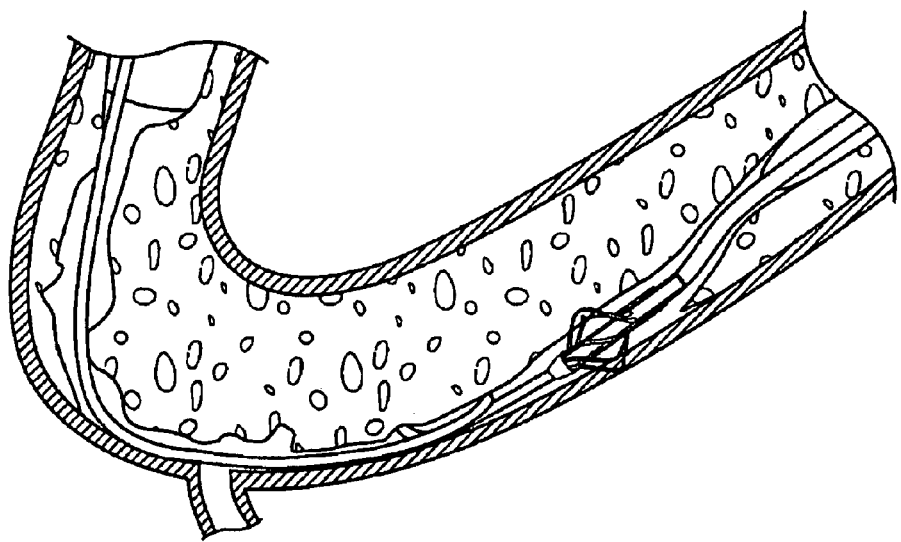
Figure 7C:
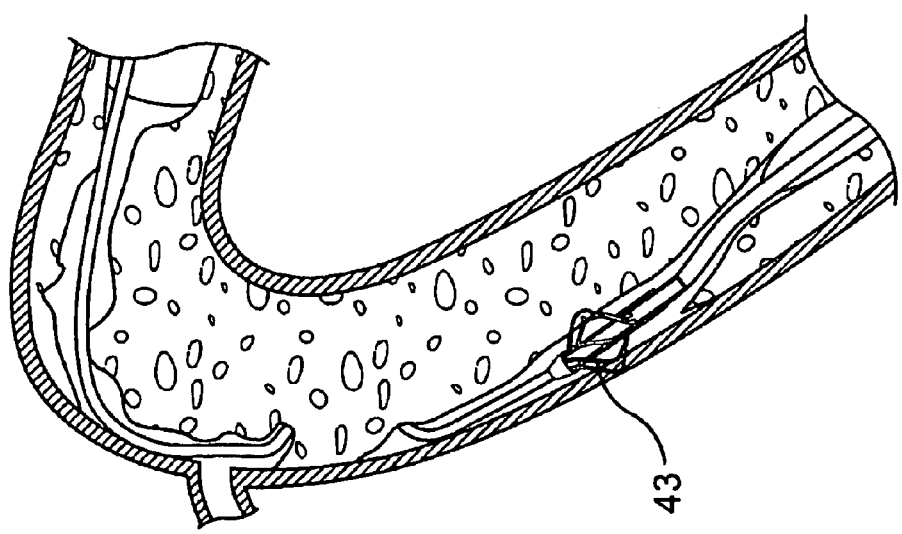
Figure 7F:
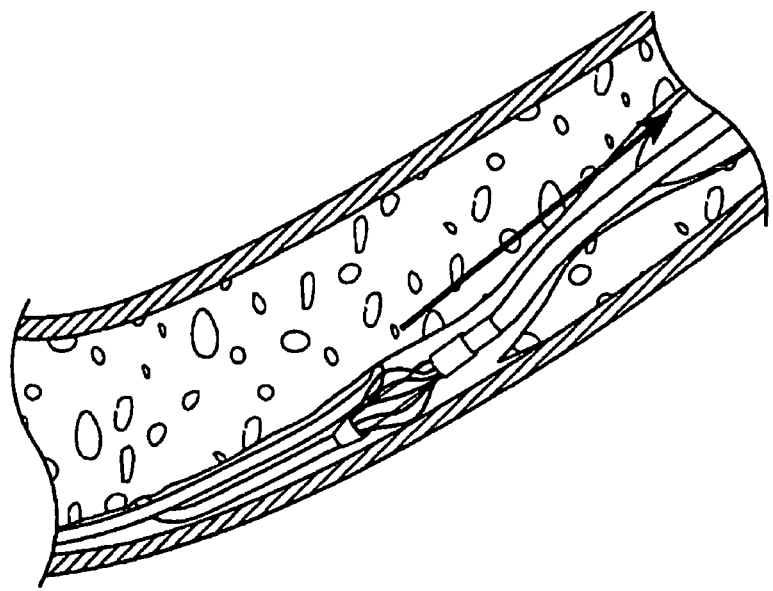
Figure 7E:
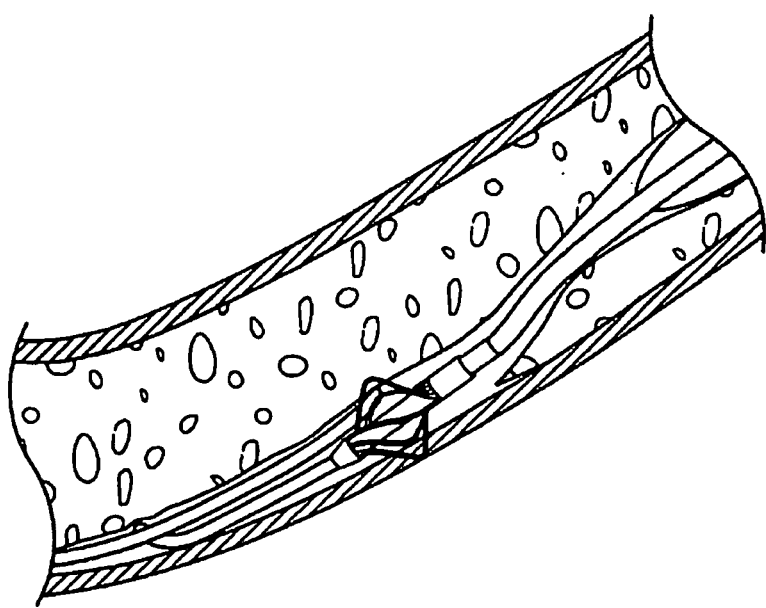

FIGS. 7A-7F show how the capture devices shown in FIG. 5 could be used in practicing the CART technique. As shown in FIG. 7A, an antegrade guidewire 710 is placed in the proximal end of the occlusion, a retrograde guidewire 720 is advanced through the distal end and a balloon 730 is dilated to create space in the subintima. The device 40 shown in FIG. 5A is then advanced into the space created by the balloon dilatation (FIG. 7B). By pulling back on the inner shaft 30 (or pushing the outer shaft 41) the ribs 43 flare out creating a basket like structure (FIG. 7C). The antegrade wire, which has already been advanced through part of the occlusion is now further advanced (under fluoroscopic guidance) towards the deployed basket (FIG. 7D). Once snared into the flared ribs (basket), as shown in FIG. 7E, the ribs are allowed to close (FIG. 7F). The antegrade and retrograde wires now appear as a combined unit that is then pulled towards the distal end of the occlusion into the distal lumen. This accomplishes the goal of traversing the antegrade wire through the occlusion and recanalizing the occlusion.

The catheter with the distal end containing the flarable ribs could be about 20-200 cm long, about 0.006 to 0.035 inch guidewire compatible and have an outer diameter of about 1.5-5.0 Fr and the ribs, in their undeployed state could be about 2 to 40 mm long.

As can be easily understood, the slidable sleeve 40 (FIGS. 5A and 5B) could also be deployed in an antegrade fashion. Similar to the approach described above, where the slidable sleeve 40 is advanced over the retrograde guidewire, the slidable sleeve could also be advanced over the antegrade wire instead of the retrograde wire. Once a channel has been created by the balloon dilatation, as shown in FIG. 7B, the slidable sleeve is advanced over the antegrade wire in the channel created by the dilatation. When the physician concludes that the slidable sleeve has reached a convenient location, the ribs are deployed. Advancing the retrograde wire further allows the flared ribs to capture the retrograde wire. Upon closing the ribs, the antegrade and retrograde wires are now combined allowing the physician to maneuver the combined unit and create a continuous path or channel in the occlusion and thereby recanalizing the occlusion.

Another embodiment of the capture mechanism could be magnetic elements at the distal tips of the antegrade and retrograde longitudinal members. If the magnetic elements possess opposite polarities, as the antegrade and retrograde members approach each other the magnetic elements would be attracted to each other and force the antegrade and retrograde members to connect with each other. This would facilitate drawing the antegrade member through the occlusion and creating a continuous path or channel in the occlusion and thereby recanalizing the occlusion.

It should be noted that the capture devices described here can also be mounted on a balloon catheter and deployed in conjunction with a balloon.

In carrying out the objects of the invention as set out in the previous embodiments, it has been found that certain tools enhance the ease of practicing the CART technique. One such situation is when the channel necessary to access the CTO (either retrogradely or antegradely) may not be ideally suited for advancing the ancillary devices (such as the capture device) used to treat them. This may be due to size, tortuosity, or integrity of the channel. One such special tool is a dilating device that is used to enlarge the channel through which the capture device must traverse. Another example of a special tool is an injection device to provide a roadmap and assist in visualizing the channels.

Figure 8A:
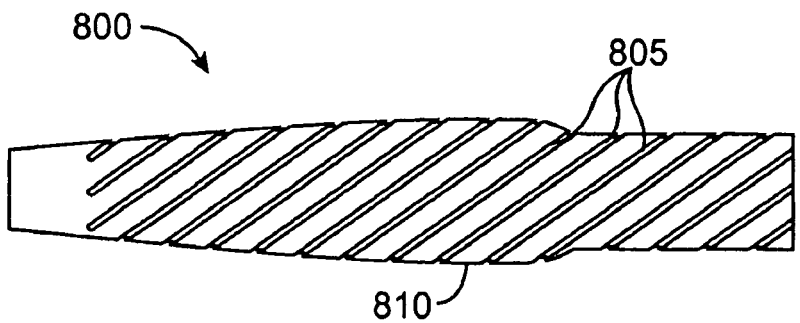
FIGS. 8A through 8C show different views and embodiments of the dilating device.

FIG. 8 shows two embodiments of the dilating device (also referred to as a septal dilator). One embodiment of the dilating device shown in FIG. 8A consists of a tapered, specially shaped plastic tube 800 with helical grooves 805 that can be advanced over the retrograde guidewire, to enlarge or dilate the intercoronary channels, and occasionally the occlusion itself. The tapered enlarged portion 810 extends typically 2-20 mm with a maximum diameter of 6.0 mm. The wall thickness at the tip is, typically, 0.10 to 1.0 mm. In practice, once the septal that needs to be dilated has been identified, the physician would slowly advance the dilator by gently turning, twisting or pushing the dilator that is riding over the guidewire. The grooves in the thin-walled plastic tube would work like the grooves on a screw and advance the dilator over the guidewire, while simultaneously enlarging the channel.

Figure 8B:
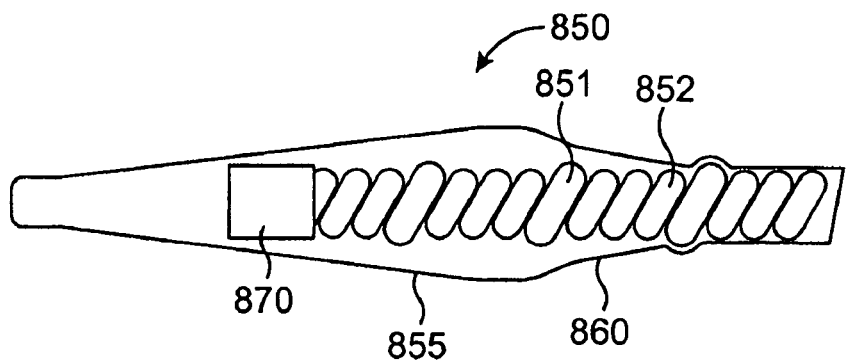
Figure 8C:
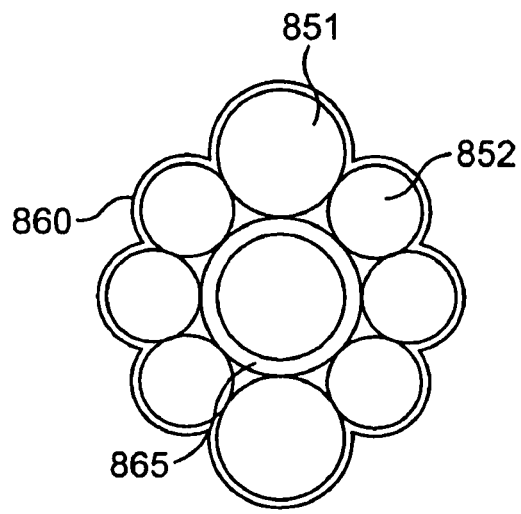

Another embodiment of the dilating device is shown in FIGS. 8B and 8C. This dilating device 850 consists of 8 wires (but the number of wires can range from four to twenty) wound around a central PTFE liner 865 with a polymer tip region 855. Tip 855 is about 2-20 mm long at the distal end of the device and is narrowest at the most distal tip of the device. At least two of the wires 851 that are arranged at diametrically opposite locations, are of a slightly larger diameter than the other six wires 852 along the distal end of the dilating device 850. Similar to the role of the helical grooves 805 shown in FIG. 8A, the combination of the large and small wires (851 and 852) enables advancement of the dilating device when the device is gently twisted over the guidewire. The diameter of the smaller wires can range from 0.01 mm to 1.0 mm with a typical size of 0.08 mm and the diameter of the larger wires can range from 0.02 mm to 2.0 mm with a typical size of 0.13 mm. The length of the helical groove is typically about 200 mm, but can run the entire length of the dilating device which can range from 20-300 cm. The dilating device 850 is encapsulated within polymer jacket 860 along at least part of its length to modify the flexibility of the dilating device 850 and to enable smooth passage through the body lumen. Alternatively, the dilating device 850 could also be coated with a hydrophilic polymer. The PTFE liner 865 typically has an ID of 0.43 mm, but can range from 0.15-1.0 mm, while the dilating device has an OD of 0.83 mm, but can range from 0.5-2.0 mm. In another embodiment of the dilating device 850, the number of wires wound around the central liner can range from 3-20 with each being of similar diameter. Optionally, any of the dilating devices described herein may comprise an atraumatic distal tip.

The use of a dilating device enlarges and prepares the channel (usually the septals) to more readily permit advancement of subsequent ancillary devices including, for example, the injection device and the capture device. A wider lumen improves device crossability through the channel and/or CTO and may also improve safety by remodeling or "straightening" the channel to facilitate device advancement and withdrawal. In cases where the dilating device is also used for injecting contrast, it can aid in visualizing a roadmap of the channels (super-selective injections).

Figure 9A:
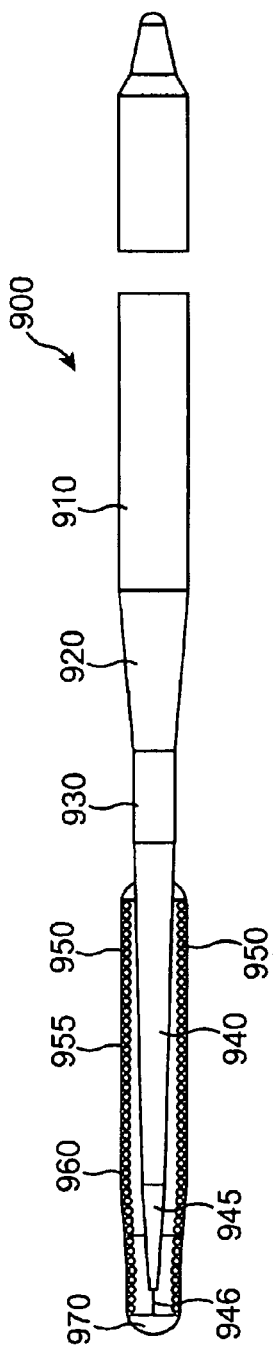
FIGS. 9A and 9B show a guidewire suitable for the CART technique with radiopaque coil and 3-D pre-shaped tips.

Another special tool that can improve the procedure time and ease of performing the CART technique is a retrograde guidewire. The special retrograde guidewire is useful in navigating extremely narrow and tortuous vessels. One embodiment of the retrograde guidewire is shown in FIG. 9A. This flexible guidewire 900 consists of an elongated core with a proximal section 910, a tapering distal section 940 and sections 920 and 930 that transition the proximal section 910 to the distal section 940. Section 940 further extends distally into a conical section 945 which in turn is connected to the distal tip 970 by means of a ribbon 946 using standard connecting techniques known in the art. Almost the entire section distal to section 930, starting with section 940 and ending up to the tip 970 is surrounded by a tapered helical coil 950. This distal section that is surrounded by the helical coil is also covered by a polymer sheath or jacket 955, typically polyurethane, which in turn is covered by a hydrophilic coating 960. The helical coil 950 extends up to the proximal edge of the distal tip 970. The sheath 955 and the hydrophilic coating 960 extend all the way to the outermost tip of the flexible guidewire.

The helical coil 950 is typically made of radiopaque materials such as platinum, iridium, palladium, tungsten and alloys thereof. The core can be formed of materials with high strength such as stainless steel or Ni—Ti alloys.

The guidewire 900 can be up to 350 cm long and 0.008-0.035 inches in diameter with the radiopaque portion 950 extending to about 160 mm in length. Occasionally, the entire length of the guidewire can be radiopaque. The radiopaque coil portion 950 is about 0.012-0.014 inches diameter for about 110 mm (covering section 940) towards the distal tip and then it tapers down to about 0.006-0.009 inches for approximately 5-160 mm covering the conical section 945 and up to the proximal edge of 970. The abruptly tapered construction of the guidewire confers a unique flexibility so that fine, tortuous lumens can be accessed.

Figure 9B:
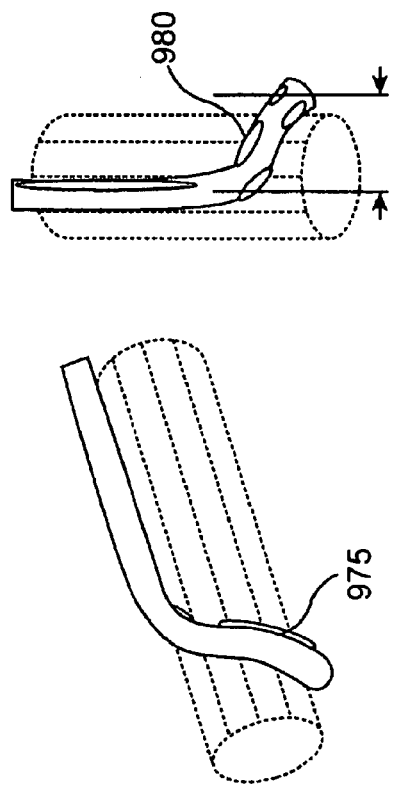

Another aspect of the retrograde guidewire is shown in FIG. 9B in which the distal tip is shaped into a 3-D configuration to further facilitate advancement through tortuous and/or narrow vessels, particularly the septals. Normally, the physician bends the distal tip of the guidewire 900, if it is not already bent, to navigate the tortuous and branching vasculature. The embodiments shown in FIG. 9B show preshaped tip configurations 975 and 980 that facilitate advancing the guidewire through tortuous and branching vessels. Distal tips 975 and 980 are preshaped orthogonally anywhere from approximately 2 to 20 mm from the distal end and then again at approximately 4 to 20 mm from distal end. Angle of bend can range anywhere from 0 to 180 degrees. Diameter at distal end of guidewire can be tapered down to as much as 0.006 inches.

The performance of a guidewire (180 cm long and about 0.014 inches in diameter) with the radiopaque coil was tested using standard techniques. One measure of performance of a guidewire is the angle of rotation at the distal tip when the proximal tip is rotated. An ideal guidewire would have a one-to-one translation: for one rotation of the guidewire at the proximal end, the distal end should go through one rotation. For the guidewire shown in FIG. 9, the angle of rotation of the distal tip as a function of rotation provided at the proximal end was found to be comparable to that of a commercially available guidewire. The tip flexibility of the inventive guidewire was also found to be comparable to that of the commercially available guidewire.

As described in the schematic procedure for the CART technique (FIG. 1), occasionally, the septals may not be easily identifiable to pursue the CART technique. Injecting contrast agents at the appropriate location may reveal the available septals. The injection device shown in FIG. 10 is used to super-selectively inject contrast into the intercoronary channel to facilitate identification of an appropriate channel while simultaneously advancing and manipulating the guidewire. Alternatively, the injection device may be used to inject a therapeutic agent to a septal or treatment site.

Figure 10A:
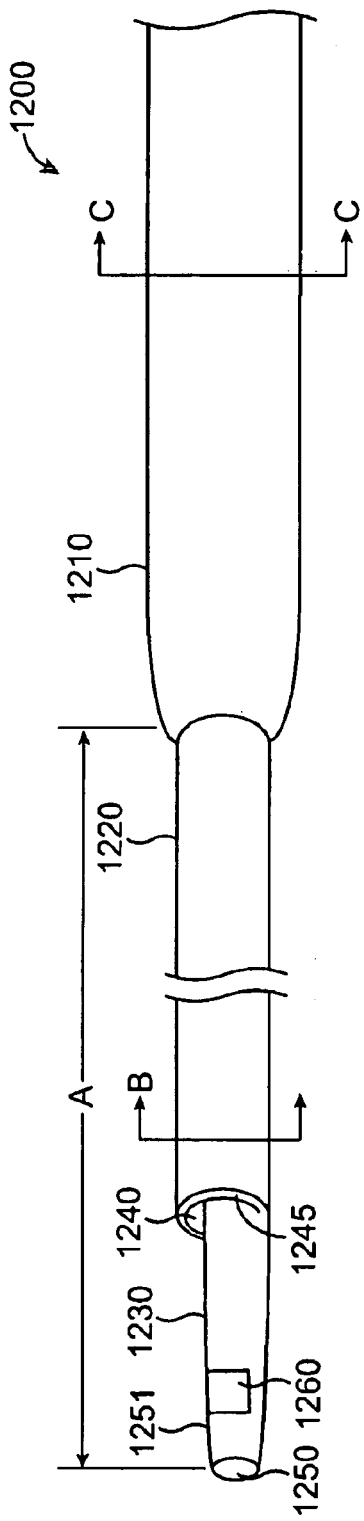
FIGS. 10A through 10C show various views of an injection device.

An embodiment of an injection device is shown in FIG. 10A. Catheter 1200 is a multilumen catheter comprising catheter shafts 1210, 1220 and 1230. The inner shaft 1230 (guidewire shaft) is defined by guidewire lumen 1250 and a thin wall 1251. Injection port 1240 is defined by the wall 1251 of the inner shaft 1230 and wall 1245 of shaft 1220. Inner shaft 1230 extends the entire length of catheter 1200. To facilitate identification of the location of the injection catheter 1200, inner shaft 1230 contains a radiopaque marker 1260 adjacent to the distal tip of inner shaft 1230.

Figure 10C:
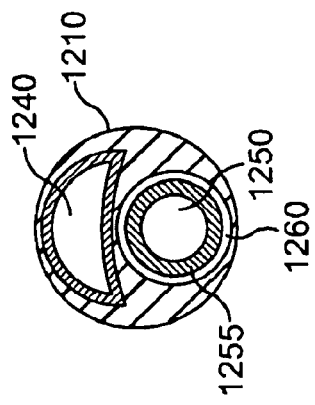
Figure 10B:
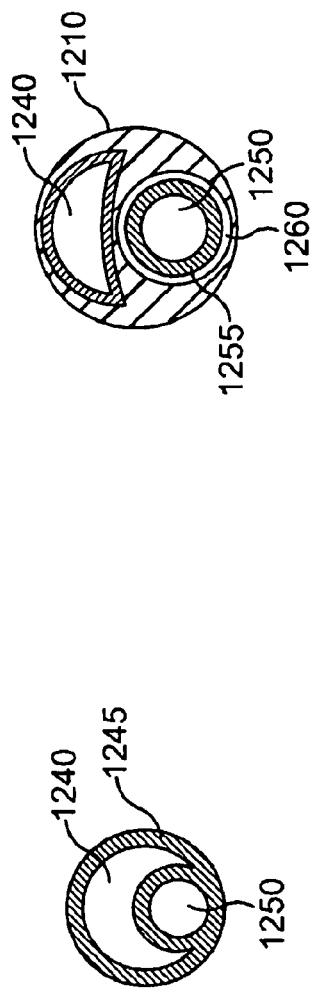

FIG. 10B shows the cross-section of shaft 1220. FIG. 10C shows the cross section at the proximal end of the catheter 1210. Each of shafts 1210, 1220 and 1230 can be made of any number of polymers including but not limited to nylon, PEBAX, polyurethane, polyethylene and polyimide. Contrast agent that is injected at the proximal end of the catheter exits the injection port 1240. FIG. 10C also shows the guidewire lumen 1250 and a guidewire channel with an optional braided lining 1260 and an optional PTFE lining 1255. A typical ID for the guidewire lumen 1250 would be about 0.39 mm but can range from 0.15-1.0 mm. A typical OD for the catheter shaft 1230 would be 0.83 mm but can range from 0.5-2.0 mm.

It should also be noted that each device, the guide wire, capture device, dilating device and the injection catheter, can be used independently or in conjunction with one or more of the listed devices. For example, the guidewire shown in FIG. 9 can operate with the injection device of FIG. 10 or the capture device apart from being used similar to a traditional guidewire.

Often, the passageways to the septals or treatment sites may be tortuous and impede the progress of an injection catheter. Therefore, the multilumen injection catheters described above may be modified for improved maneuverability. In an alternative embodiment of the injection catheter, two shafts are detached from each other but are contained coaxially within one another. In such an embodiment, the inner shaft is the guidewire shaft, and the outer shaft is an injection shaft. An injectate is injected proximally into a supply port, travels through the space between the two coaxial shafts, and flows distally out of an injection port. This coaxial arrangement allows the two lumens to retain their functionality, while decreasing the rigidity that would be created by an attached multilumen configuration. Furthermore, having the injectate and the guidewire in separate lumens further enhances guidewire maneuverability. The added maneuverability and flexibility decreases the likelihood of the injection catheter kinking as it navigates tortuous pathways, thereby allowing for improved access to treatment sites as well as improved delivery of contrast or diagnostic agents or therapeutics to such sites.

Figure 11A:
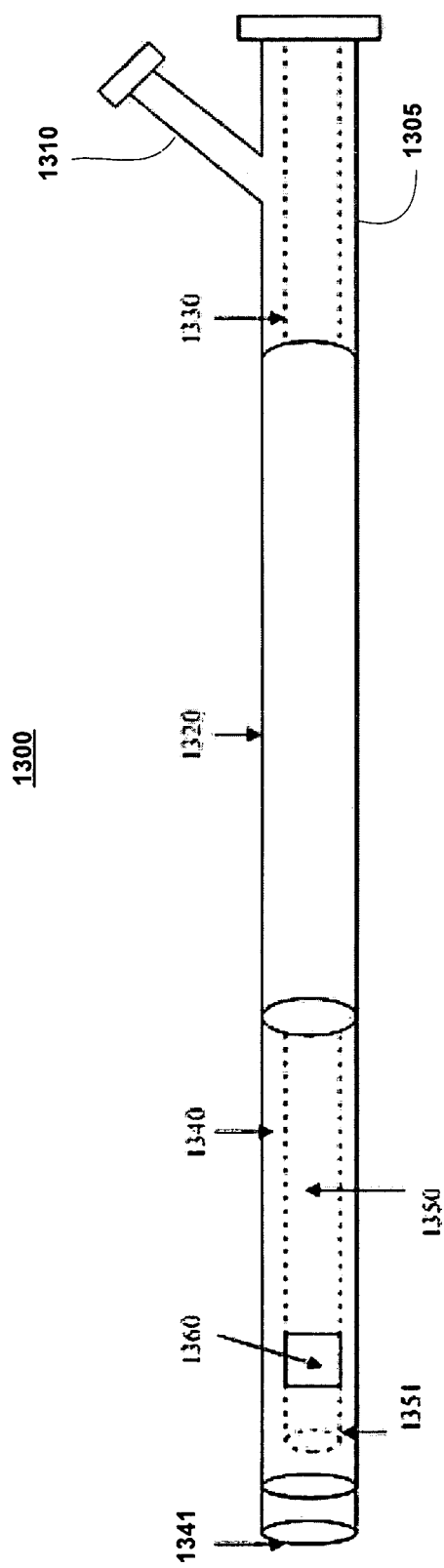
FIGS. 11A through 11F show another embodiment of an injection device comprising coaxial shafts.

FIG. 11A shows an exemplary embodiment of such an injection device having a coaxial multilumen configuration. Injection device 1300 comprises a hub 1305, an injection shaft 1320, and an inner guidewire shaft 1330. The inner diameter of injection shaft 1320 is larger than the outer diameter of guidewire shaft 1330, such that guidewire shaft 1330 resides coaxially within injection shaft 1320, but is not attached to injection shaft 1320. The proximal end of guidewire shaft 1330 is coupled to hub 1305, whereas the distal end of the guidewire shaft 1330 is free-floating within injection shaft 1320. Injection shaft 1320 comprises a wall 1341 and an injection shaft lumen 1340. Guidewire shaft 1330 comprises a wall 1351 and a guidewire lumen 1350. Hub 1305 comprises an injectate supply port 1310 that feeds into the space between the injection shaft wall 1341 and the guidewire wall 1351. An injectate, when injected proximally into supply port 1310, travels through the space between the two shaft walls 1351 and 1341, and flows distally out of the injection device 1300. Optionally, the distal tip of the guidewire shaft 1330 or the injection shaft 1320 may comprise a radiopaque marker 1360, as shown.

In the embodiment shown in FIG. 11A, the length of guidewire shaft 1330 is shorter than the length of injection shaft 1320. Alternatively, the length of guidewire shaft 1330 may be longer than the length of injection shaft 1320, or the same length as the injection shaft 1320.

Figure 11B:
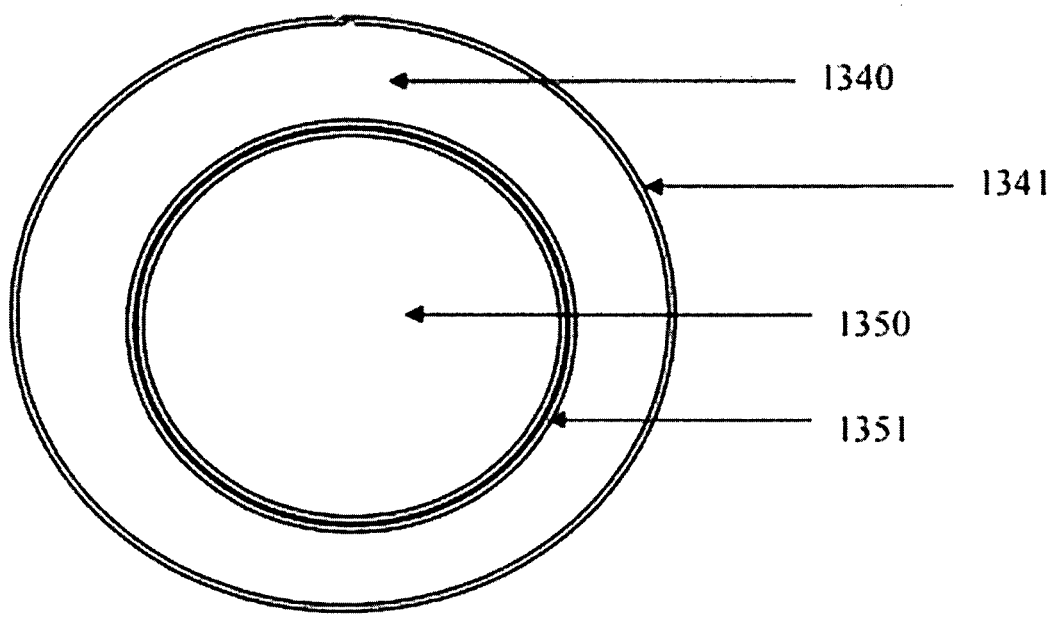

FIG. 11B shows a cross-section of the injection device of FIG. 11A, showing injection and guidewire shaft walls 1341 and 1351, and injection and guidewire lumens 1340 and 1350. Each of the shaft walls 1341 and 1351 may be made of one or more polymers, including but not limited to nylon, PEBAX, polyurethane, polyethylene and polyimide. Optionally, the inside of the guidewire shaft wall 1351 is lined with a material having a low coefficient of friction, for example PTFE or high-density poly-ethylene, to facilitate movement of the guidewire within the guidewire lumen 1350.

Optionally, the guidewire shaft 1330 and/or the injection shaft 1320 may comprise a plurality of segments made of materials with differing durometers, thereby allowing finer control of the flexibility along the length of the shaft. For example, in one embodiment, the proximal end of the guidewire shaft 1330 may comprise a braid, increasing the rigidity and allowing a user to advance the injection device by providing a force proximally, whereas the distal end of the guidewire shaft 1330 may comprise a coil, increasing the flexibility and allowing the injection device to follow tortuous passageways without kinking. Optionally, the leading edge of the injection device may comprise a soft tip to promote maneuverability and prevent damage to the vessel wall.

Figure 11C:
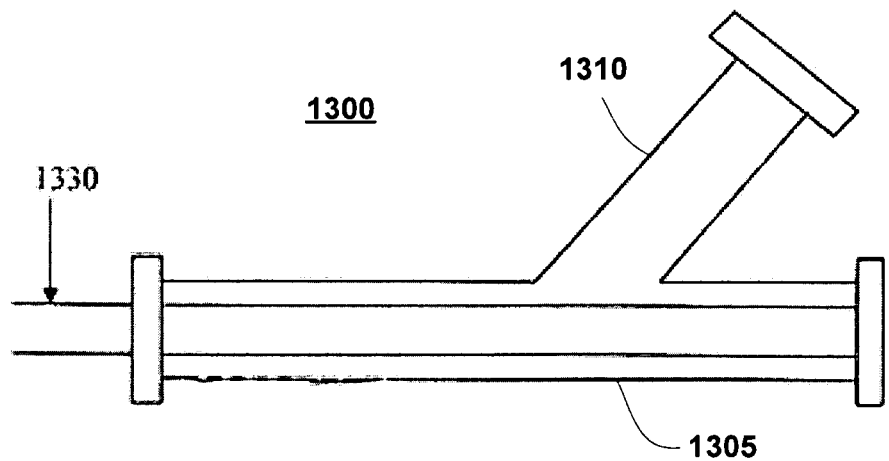
Figure 11D:
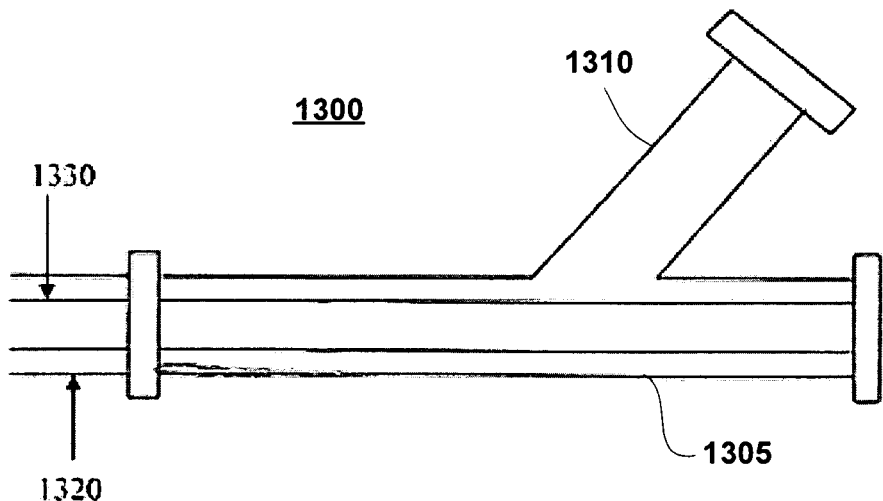

Hub 1305 may be permanently attached to the guidewire shaft 1330, or it may alternatively be configured to allow an injection shaft 1320 to be detachably attached to the hub 1305. FIGS. 11C and 11D show examples of both such embodiments. FIG. 11C shows an embodiment of the hub 1305 comprising a supply port 1310 and a permanently attached guidewire shaft 1330, but without an attached injection shaft 1320. In this embodiment, the hub 1305 is configured to accept a detachable attachment of an injection shaft 1320. This allows the hub 1305 to be used with different injection shafts, for example with disposable injection shafts, with injection shafts of differing lengths, or with injection shafts having different flexibility or rigidity characteristics. Alternatively, hub 1305 may be permanently attached to an injection shaft 1320, as shown in FIG. 11D. In both embodiments, the injection shaft 1320 may be a microcatheter or any other shaft structure.

Figure 11E:
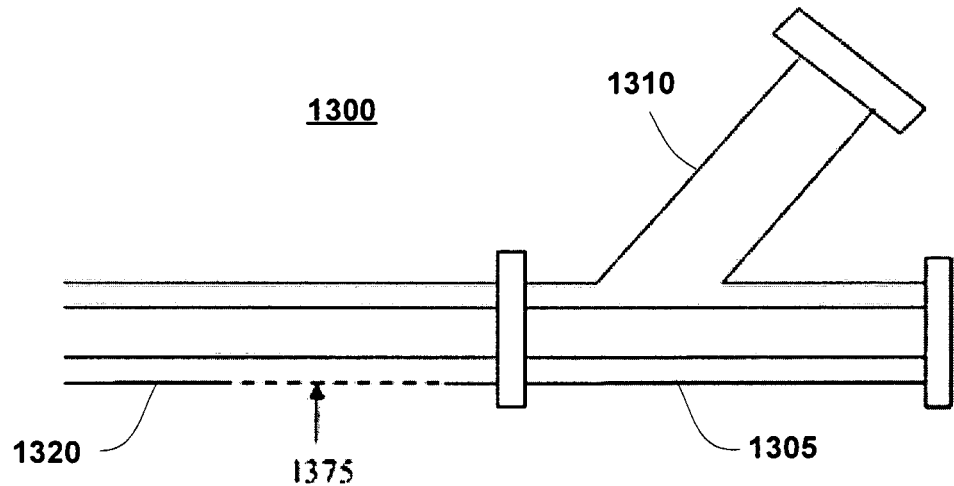
Figure 11F:
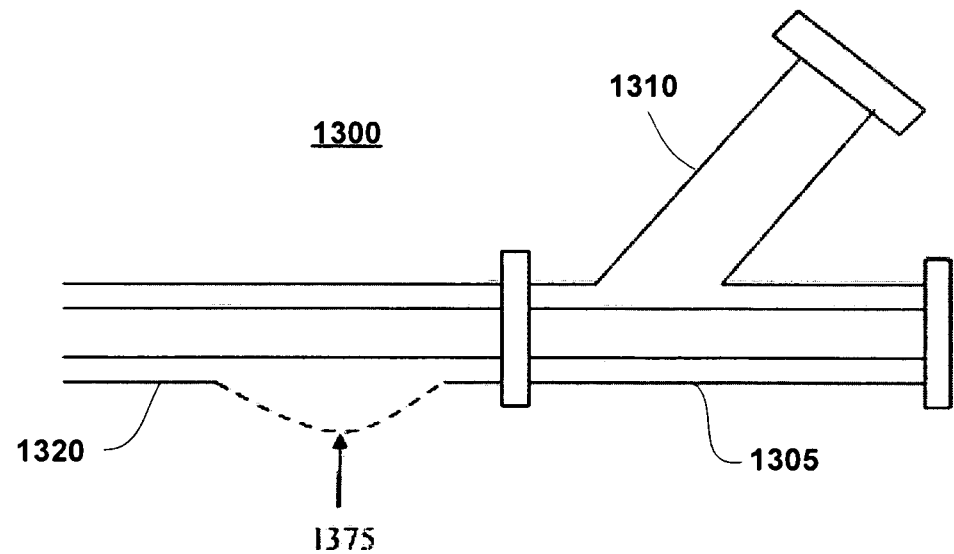

In an optional embodiment, the hub may comprise an expandable injectate reservoir. Upon injection of an injectate into the supply port of the hub, the injectate flows into and expands the reservoir. The reservoir stores the injectate and thereby allows a more steady injectate flow within and along the length of the injection shaft. FIGS. 11E and 11F show such an embodiment. FIG. 11E shows an injection device 1300 comprising an injectate reservoir 1375 on the outside of the injection shaft wall. As an injectate is injected into the supply port 1310, some of the injectate flows into the reservoir 1375, causing the reservoir 1375 to gradually fill and expand, as shown in FIG. 11F. The pressure of the expanded reservoir 1375 then contributes to a more steady injectate flow along the length of the injection device 1300. In an alternative embodiment, the reservoir 1375 may be positioned on the inside of the injection shaft 1320, or on the hub 1305.

Optionally, supply port 1310 is pressurized to facilitate a continuous flow of the injectate. For example, supply port 1310 may be coupled to an external device, such as an intravenous drip bag, a pressurized intravenous drip bag, or a locking syringe. Supply port 1310 may be configured to lockingly couple with such an external device. Alternatively, a hub is configured with a supply port and a reservoir, allowing the hub to be used with any catheter (such as a microcatheter, a balloon catheter, etc.).

EXAMPLE

Materials and Methods and Procedure Description

All patients enrolled were treated with the CART technique, either as the primary option or following a failed antegrade attempt with conventional or dedicated wires, during the same or prior procedure. Indication for CTO revascularization was either symptoms of angina or proven stress-induced ischemia. The duration of the occlusion was estimated from previous angiographic data or from clinical information (acute myocardial infarction or sudden change in angina pattern) or ECG changes consistent with the location of the occlusion.

The procedure was performed using the controlled antegrade and retrograde approach. As described earlier, the retrograde approach uses an intercoronary channel which can be either an epicardial channel, inter-atrial channel, an intraseptal channel (septal collateral), or a bypass graft. It is rather uncommon to find an epicardial intercoronary collateral that has a suitable morphology for use as a connecting channel. However, frequently, a review of the angiogram allows one to find a septal channel in most CTO cases, particularly in the LAD or RCA.

In treating the patients in the study using the CART technique, a wire was initially advanced antegradely from the proximal true lumen into the CTO and then into the subintimal space at the CTO site. By monitoring the resistance of the wire tip or wire movement, the operator can ascertain when the wire has entered the subintima. Next, another wire was advanced through the intercoronary collateral using a microcatheter. This wire was placed at the distal end of the CTO, and then penetrated retrogradely from the distal true lumen into the CTO, and then into the subintima at the CTO site. After advancing a small balloon (1.5-2.0 mm) over the retrograde wire into the subintima, the balloon was inflated. In order to keep this subintimal space open, the deflated balloon was left in place. Consequently, the two dissections created by the antegrade wire and the retrograde balloon were in the subintima at the CTO site, and this allowed both of them to connect easily. Thereafter, the antegrade wire was advanced further along the deflated retrograde balloon which extended from the subintimal space to the distal true lumen. After successful recanalization, dilatation and stent implantation were performed. Suitable materials recommended for the CART technique are summarized in Table 1.

TABLE 1

Materials for CART Technique

| | |
|---|---|
| Guiding catheter: | short guiding catheter (80-85 cm) brachial approach might be required in tall patients 6 or 7 French |
| Wire: | Polymer wire with hydrophilic coating for the navigation through the tortuous intercoronary channel |

TABLE 1-continued

Materials for CART Technique

| | |
|---|---|
| Micro-catheter: | super-selective injection may be necessary to identify suitable channel required for step by step wire navigation and protection of the intercoronary channel |
| Balloon: | low profile balloon size from 1.5 to 2.5 mm |

DEFINITIONS

Coronary chronic total occlusion is defined as a true total occlusion if the thrombolysis in myocardial infarction (TIMI) was grade 0 flow. Total occlusions of duration greater than 3 months were considered chronic.

Angiographic success was defined as restoration of antegrade flow, with a TIMI grade 3 flow, and also a final residual stenosis less than 30%.

In hospital major adverse cardiac events (MACE) were defined as death, non-Q and Q-wave MI, or the need for target vessel revascularization (TVR).

Statistical Analysis

Descriptive analyses were used. Results are either quoted as percentages for categorical data or as mean± standard deviation for continuous variables.

Results

Ten patients (9 males, 1 female) with CTO of native coronary arteries were treated with the CART technique. Patient characteristics are summarized in Table 2. Baseline lesion characteristics are shown in Table 3. CTO duration varied from 7 to 84 months. All CTOs were total occlusions with a TIMI 0 flow. In 8 of the 10 cases, it was a repeat treatment attempt. Procedural characteristics and results are shown in Table 4.

Vessel recanalization with a TIMI 3 flow in the distal true lumen was achieved in all 10 cases. Drug eluting stents were implanted in all but two cases. The intercoronary collateral used for the retrograde approach was a septal branch in 4 cases, a collateral between the circumflex artery and the postero-lateral branch (PL) of the distal right coronary artery (RCA) in 5 cases. In one case, the retrograde approach was performed through a bypass graft (gastro-epiploic artery) to the posterior descending artery of the RCA. The size of the balloon used retrogradely ranged from 1.5 to 3.0 mm, and the inflation pressure for the dilatation of the subintimal space ranged from 6 to 18 atmospheres. No complications such as perforation or occlusion occurred in the collateral channel. In all cases, the subintimal dissection was limited to the CTO region. There was no in-hospital death, myocardial infarction or emergent target vessel recanalization.

TABLE 2

Baseline Patient Characteristics

| | |
|---|---|
| Age (years) | 63.9 ± 10.9 |
| Male (%) | 9 (90) |
| Prior MI (%) | 6 (60) |
| Prior CABG (%) | 1 (10) |
| 3-VD (%) | 5 (50) |
| 2-VD (%) | 3 (30) |
| 1-VD (%) | 2 (20) |
| LV EF % | 0.52 ± 0.12 |
| Diabetes (%) | 5 (50) |

TABLE 2-continued

Baseline Patient Characteristics

| | |
|---|---|
| Hypertension (%) | 8 (80) |
| Hyperlipidemia (%) | 7 (70) |
| Smoker (%) | 6 (60) |

MI = myocardial infarction,
CABG = coronary artery bypass graft,
VD = vessel disease,
LV EF = left ventricular ejection fraction.
Continuous values are expressed as mean ± standard deviation.

TABLE 3

Baseline Lesion Characteristics

| Case | Vessel | CTO duration (months) | Mor- phology | Calcification | Bridging collateral | Length (mm) |
|---|---|---|---|---|---|---|
| 1 | RCA | >36 | T | No | no | >60 |
| 2 | RCA | >14 | A | No | yes | >60 |
| 3 | RCA | >24 | A | No | no | >60 |
| 4 | RCA | >84 | T | Moderate | yes | >60 |
| 5 | RCA | >72 | A | Moderate | yes | >60 |
| 6 | LAD | Unknown | A | Mild | no | 20 |
| 7 | RCA | >7 | A, SB | Moderate | yes (faint) | 10 |
| 8 | RCA | Unknown | A, SB | Mild | no | 20 |
| 9 | RCA | >27 | A | Moderate | yes | 20 |
| 10 | RCA | >14 | A | Moderate | yes | 20 |

RCA = right coronary artery,
LAD = left anterior descending artery,
T = tapered,
A = abrupt,
SB = side branch at the occlusion site,
CTO = chronic total occlusion.

TABLE 4

Procedural characteristics and results

| Case | Success | Collateral used | Size of retrograde guiding catheter (Fr) | Size of retrograde Balloon (mm) | Retrograde inflation pressure (atm) | Retrograde wire | Antegrade wire |
|---|---|---|---|---|---|---|---|
| 1 | yes | LCX→AC→PL | 7 | 1.5→2.5 | 14 | CPT | M 3 g |
| 2 | yes | LCX→AC→PL | 6 | 1.5→3.0 | 8 | CPT → M 3 g | C 9 g |
| 3 | yes | LCX→AC→PL | 6 | 1.5→2.5 | 8 | CPT | M 12 g |
| 4 | yes | LCX→AC→PL | 6 | 2.5 | 6 | F → M 2 g | M 3 g |
| 5 | yes | LCX→AC→PL | 7 | 2.0 | 12 | F → M 3 g | C 9 g |
| 6 | yes | PD→S→LAD | 6 | 1.5→2.0 | 16 | F → M 3 g | M 3 g |
| 7 | yes | GEA→PD | 6 | 2.0→2.5 | 12 | F → M 3 g | M 3 g |
| 8 | yes | LAD→S→PD | 6 | 2.0→2.5 | 18 | F → M 3 g | M 12 g |
| 9 | yes | LAD→S→PD | 7 | 2.0 | 12 | F → M 3 g | C 12 g |
| 10 | yes | LAD→S→PD | 7 | 1.5 | 12 | F → M 3 g | M 4.5 g |

LCX = left circumflex artery,
LAD = left anterior descending artery,
PL = postero-lateral artery,
PD = posterior descending artery,
AC = atrial circumflex collateral,
GEA = gastro-epiploic artery,
Fr = French,
mm = millimeter,
atm = atmosphere,
g = gramme,
M = Miracle,
C = Confianza,
CPT = Choice PT floppy,
F = Fielder.

The above results show that use of the CART technique can help the physician successfully recanalize difficult to cross CTOs.

While the invention has been disclosed with reference to certain embodiments, it will be understood by those skilled in the art that various changes may be made and equivalents may be substituted without departing from the scope of the invention. Particularly, while the examples have illustrated the use of the CART technique in occluded coronary arteries, it should be noted that the disclosed invention is not limited to coronary occlusions but is applicable to other examples of occlusions, e.g., peripheral arteries and peripheral arterial diseases and CTOs related to those could also be treated using the devices and technologies described here. Furthermore, it should be understood that a purely retrograde approach would also be a viable approach to recanalize an occlusion. In such cases, a subset of the devices, e.g., the flexible guidewire and septal dilator may be adequate for recanalization. A capture device may not be necessary and an injection catheter may or may not be used. In addition, many modifications may be made to adapt to a particular situation or material to the teachings of the invention without departing from its scope.

Additionally, the individual components of the CART technique are not limited to coronary occlusions. It should be noted, for example, that the injection catheter may also be used as a mechanism to deliver therapeutic or diagnostic agents to any site within the vascular system. For example, in oncology, one or both of the injection catheter and dilating catheter may be used to inject a drug (e.g., 5FU, doxorubicin, adriamycin, etc.) at the site of a tumor. As another example, in interventional neuroradiology, one or both of the injection catheter and dilating catheter may be used to diagnose or treat aneurysms or fistulas by delivering therapeutic or diagnostic agents including coils, polymers, gels, etc.

Either or both the injection catheter and dilation catheter may be used for the treatment or diagnosis of other passageways in the body. Dialysis patients, for example often have shunts that get occluded. The dilation catheter, the injection catheter, or both in combination, may be used to create a channel or to inject thrombolytics.

The dilation catheter, the injection catheter, or both in combination, may be used to create a channel or deliver a drug in any passageway or occluded lumen in the body. Thus, these catheters may be used for treating occlusions or stenosis in bile ducts, urethral passageways, lymphatic ducts, pulmonary passageways, renal ducts, fallopian tubes, etc.

Additionally, the dilating catheter may be utilized as a transport mechanism for stiff inner components that are used to provide therapy, tissue ablation, etc., such as fiber optic components. Presently, fiber optic wires when used without a flexible support structure may break when introduced into tortuous bodily passageways. The flexibility of the dilating catheter or the injection catheter allows for easier movement of fiber optic components along the internal lumen of the catheters.

What is claimed is:

1. A dilating device for enlarging a vessel, comprising:
a longitudinal member having a distal end and a proximal end and having a guidewire shaft defined by a guidewire lumen, wherein the longitudinal member comprises a plurality of wires and wherein the wires are of at least two diameters and at least two of the wires are located at diametrically opposing locations at the distal end of the longitudinal member and have a larger of the at least two diameters than at least one other of the wires at the distal end of the longitudinal member;
wherein the wires are encapsulated within a jacket; and
wherein the jacket has an increasing tapered configuration along at least part of its length between a tip at a distal end of the jacket toward a proximal end of the jacket to enable advancement of the longitudinal member through a narrow diameter blood vessel by gradually enlarging the vessel diameter using the tapered configuration of the jacket.

2. The dilating device of claim 1, wherein the longitudinal member comprises a helical exterior.

3. The dilating device of claim 1, wherein the plurality of wires are configured to be wound around a liner.

4. The dilating device of claim 1, wherein the longitudinal member comprises an atraumatic distal tip.

5. The dilating device of claim 1, wherein the longitudinal member comprises at least one radiopaque marker.

6. The dilating device of claim 3, wherein the liner comprises polytetrafluoroethylene (PTFE) or high density polyethylene (HDPE).

7. The dilating device of claim 1, wherein the jacket is a polymer jacket and enables smooth passage through the vessel.

8. The dilating device of claim 1, wherein the longitudinal member is configured to deliver a therapeutic or diagnostic agent.

* * * * *